US012558424B2

(12) United States Patent
Leonard et al.

(10) Patent No.: US 12,558,424 B2
(45) Date of Patent: Feb. 24, 2026

(54) T CELLS HAVING ENHANCED ANTI-TUMOR ACTIVITY

(71) Applicant: The United States of America, as represented by the Secretary, Department of Health and Human Services, Bethesda, MD (US)

(72) Inventors: Warren J. Leonard, Bethesda, MD (US); Dalton J. Hermans, Manitowoc, WI (US); Luca Gattinoni, Washington, DC (US); Leonard M. Neckers, Bethesda, MD (US); Sanjivan Gautam, Rockville, MD (US); Suman Mitra, Lambersart (FR)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 961 days.

(21) Appl. No.: 17/633,414

(22) PCT Filed: Aug. 6, 2020

(86) PCT No.: PCT/US2020/045100

§ 371 (c)(1),
(2) Date: Feb. 7, 2022

(87) PCT Pub. No.: WO2021/026290

PCT Pub. Date: Feb. 11, 2021

(65) Prior Publication Data

US 2022/0331360 A1 Oct. 20, 2022

Related U.S. Application Data

(60) Provisional application No. 62/883,927, filed on Aug. 7, 2019.

(51) Int. Cl.

| | |
|---|---|
| ***A61K 40/11*** | (2025.01) |
| ***A61K 40/42*** | (2025.01) |
| ***A61P 35/00*** | (2006.01) |
| ***C07D 231/00*** | (2006.01) |

(52) U.S. Cl.

CPC .......... *A61K 40/11* (2025.01); *A61K 40/4273* (2025.01); *A61P 35/00* (2018.01); *A61K 2239/57* (2023.05); *C07D 231/00* (2013.01)

(58) Field of Classification Search

CPC ..... A61P 35/00; A61K 40/11; A61K 40/4273; A61K 2239/57

See application file for complete search history.

(56) References Cited

U.S. PATENT DOCUMENTS

| | | | |
|---|---|---|---|
| 2017/0218042 | A1 | 8/2017 | Tran et al. |
| 2017/0224800 | A1 | 8/2017 | Tran et al. |

FOREIGN PATENT DOCUMENTS

| | | | |
|---|---|---|---|
| WO | WO 2016/109559 | A2 | 7/2016 |
| WO | WO 2017/070042 | A1 | 4/2017 |
| WO | WO 2018/005807 | A1 | 1/2018 |

OTHER PUBLICATIONS

Xie et al. Targeting Lactate Dehydrogenase-A Inhibits Tumorigenesis and Tumor Progression in Mouse Models of Lung Cancer and Impacts Tumor-Initiating Cells. Cell Metabolism (2014), 19, 795-809. (Year: 2014).*

Granchi et al. Inhibitors of Lactate Dehydrogenase Isoforms and their Therapeutic Potentials. Current Medicinal Chemistry (2010), 17, 672-697. (Year: 2010).*

Nagai et al. Cancer prevention from the perspective of global cancer burden patterns. J. Thorac Dis (2017), 9(3), 448-451. (Year: 2017).*

Yeung et al. Targeting Glycolysis through Inhibition of Lactate Dehydrogenase Impairs Tumor Growth in Preclinical Models of Ewing Sarcoma. Cancer Res (epub. Aug. 20, 2019) 79 (19): 5060-5073 plus appended PubMed Abstract (Year: 2019).*

Buck et al., "Mitochondrial Dynamics Controls T Cell Fate Through Metabolic Programming," *Cell,* 166(1): 63-76 (2016).

Buck et al., "T cell metabolism drives immunity," *The Journal of Experimental Medicine,* 212(9): 1345-1360 (2015).

European Patent Office, International Search Report in International Patent Application No. PCT/US2020/045100, mailed Oct. 23, 2020.

European Patent Office, Written Opinion in International Patent Application No. PCT/US2020/045100, mailed Oct. 23, 2020.

Finlay et al., "PDK1 regulation of mTOR and hypoxia-inducible factor 1 integrate metabolism and migration of $CD8^+$ T cells," *The Journal of Experimental Medicine,* 209(13): 2441-2453 (2012).

Gattinoni et al., "Wnt signaling arrests effector T cell differentiation and generates $CD8^+$ memory stem cells," *Nat. Med.,* 15(7): 808-813 (2009).

Gattinoni et al., "A human memory T-cell subset with stem cell-like properes," *Nat. Med.,* 17(10): 1290-1297 (2011).

Gattinoni et al., "T memory stem cells in health and disease," *Nat. Med.,* 23(1): 18-27 (2017).

Gautam et al., "The transcription factor c-Myb regulates CD8+ T cell stemness and antitumor immunity," *Nat. Immunol.,* 20(3): 337-349 (2019).

Gottfried et al., "Tumor-derived lactic acid modulates dendritic cell activation and antigen expression," *Blood,* 107: 2013-2021 (2006).

Hanada et al., "An effective mouse model for adoptive cancer immunotherapy targeting neoantigens," *JCI Insight,* 4(10): e124405 (2019).

Hermans et al., "Lactate dehydrogenase inhibition synergizes with IL-21 to promote $CD8^+$ T cell stemness and antitumor immunity," *PNAS,* 117(11): 6047-6055 (2020).

(Continued)

*Primary Examiner* — Sean C. Barron

(74) *Attorney, Agent, or Firm* — Leydig, Voit & Mayer, Ltd.

(57) ABSTRACT

The invention provides compositions and methods for using adoptive cell therapy (ACT) for treating cancer in a mammal. Cultured T-cells are provided by (a) obtaining an isolated population of T cells, and (b) culturing the isolated T cells ex vivo in the presence of a cytokine and a lactate dehydrogenase inhibitor. The cultured T-cells then can be administered to the mammal.

23 Claims, 53 Drawing Sheets

Specification includes a Sequence Listing.

(56) References Cited

OTHER PUBLICATIONS

Hinrichs et al., "IL-2 and IL-21 confer opposing differentiation programs to $CD8^+$ T cells for adoptive immunotherapy," *Blood*, 111(11): 5326-5333 (2008).

The International Bureau of WIPO, International Preliminary Report on Patentability in International Patent Application No. PCT/US2020/045100, mailed Feb. 17, 2022.

Jang et al., "The Small Intestine Converts Dietary Fructose into Glucose and Organic Acids," *Cell Metab.*, 27(2): 351-361 (2018).

Kalia et al., "Prolonged Interleukin-2Rα Expression on Virus-Specific $CD8^+$ T Cells Favors Terminal-Effector Differentiation In Vivo," *Immunity*, 32: 91-103 (2010).

Kim et al., "Regulation of Immune Cell Functions by Metabolic Reprogramming," *Journal of Immunology Research*, 2018: 8605471 (2018).

Langmead et al., "Ultrafast and memory-efficient alignment of short DNA sequences to the human genome," *Genome Biology*, 10: R25 (2009).

Lee et al., "An Integrated View of Immunometabolism," *Cell*, 172(1-2): 22-40 (2018).

Liao et al., "Opposing actions of IL-2 and IL-21 on Th9 differentiation correlate with their differential regulation of BCL6 expression," *PNAS*, 111(9): 3508-3513 (2014).

Lin et al., "The Common Cytokine Receptor γ Chain Family of Cytokines," *Cold Spring Harbor Perspectives in Biology*, 10: a028449 (2018).

Lin et al., "Critical functions for STAT5 tetramers in the maturation and survival of natural killer cells," *Nature Communications*, 8: 1320 (2017).

Loschinski et al., "IL-21 modulates memory and exhaustion phenotype of T-cells in a fatty acid oxidation-dependent manner," *Oncotarget*, 9(17): 13125-13138 (2018).

Markley et al., "IL-17 and IL-21 are superior to IL-2 and IL-15 in promoting human T cell-mediated rejection of systemic lymphoma in immunodeficient mice," *Blood*, 115(17): 3508-3519 (2010).

Mathis et al., "Immunometabolism: an emerging frontier," *Nat. Rev. Immunol.*, 11(2): 81 (2011).

Melamud et al., "Metabolomic Analysis and Visualization Engine for LC-MS Data," *Anal. Chem.*, 82(23): 9818-9826 (2010).

Metsalu et al., "ClustVis: a web tool for visualizing clustering of multivariate data using Principal Component Analysis and heatmap," *Nucleic Acids Research*, 43: W566-W570 (2015).

Noguchi et al., "Interleukin-2 Receptor γ Chain Mutation Results in X-Linked Severe Combined Immunodeficiency in Humans," *Cell*, 73: 147-157 (1993).

O'Neill et al., "A guide to immunometabolism for immunologists," *Nat. Rev. Immunol.*, 16(9): 553-565 (2016).

O'Sullivan et al., "Memory $CD8^+$ T cells use cell intrinsic lipolysis to support the metabolic programming necessary for development," *Immunity*, 41(1): 75-88 (2014).

Ozaki et al., "Cloning of a type I cytokine receptor most related to the IL-2 receptor β chain," *PNAS*, 97(21): 11439-11444 (2000).

Parrish-Novak et al., "Interleukin 21 and its receptor are involved in NK cell expansion and regulation of lymphocyte function," *Nature*, 408: 57-63 (2000).

Patten et al., "OPA1-dependent cristae modulation is essential for cellular adaptation to metabolic demand," *The EMBO Journal*, 33(22): 2676-2691 (2014).

Peng et al., "Aerobic glycolysis promotes T helper 1 cell differentiation through an epigenetic mechanism," *Science*, 354(6311): 481-484 (2016).

Rai et al., "Discovery and Optimization of potent, cell-active pyrazole-based inhibitors of Lactate Dehydrogenase (LDH)," *J. Med. Chem.*, 60(22): 9184-9204 (2017).

Robinson et al., "edgeR: a Bioconductor package for differential expression analysis of digital gene expression data," *Bioinformatics*, 26(1): 139-140 (2010).

Ross et al., "Signaling and Function of Interleukin-2 in T Lymphocytes," *Annu. Rev. Immunol.*, 36: 411-433 (2018).

Sabatino et al., "Generation of clinical-grade CD19-specific CAR-modified $CD8^+$ memory stem cells for the treatment of human B-cell malignancies," *Blood*, 128(4): 519-528 (2016).

Seo et al., "TOX and TOX2 transcription factors cooperate with NR4A transcription factors to impose $CD8^+$ T cell exhaustion," *PNAS*, 116(25): 12410-12415 (2019).

Song et al., "IRE1α-XBP1 controls T cell function in ovarian cancer by regulating mitochondrial activity," *Nature*, 562(7727): 423-428 (2018).

Spolski et al., "The $\gamma_c$ family of cytokines: fine-tuning signals from IL-2 and IL-21 in the regulation of the immune response [version 1; referees: 3 approved]," *F1000 Research*, 6(F1000 Faculty Rev): 1872 (2017).

Spolski et al., "Interleukin-21: a double-edged sword with therapeutic potential," *Nat. Rev. Drug. Discov.*, 13: 379-395 (2014).

Spolski et al., "Biology and regulation of IL-2: from molecular mechanisms to human therapy," *Nat. Rev. Immunol.*, 18: 648-659 (2018).

Su et al., "Metabolite Spectral Accuracy on Orbitraps," *Anal. Chem.*, 89(11): 5940-5948 (2017).

Sukumar et al., "Inhibiting glycolytic metabolism enhances $CD8^+$ T cell memory and antitumor function," *The Journal of Clinical Investigation*, 123(10): 4479-4488 (2013).

Tran et al., "Cancer Immunotherapy Based on Mutation-Specific $CD4^+$ T Cells in a Patient with Epithelial Cancer," *Science*, 344(6184): 641-645 (2014).

Tyrakis et al., "The immunometabolite S-2-hydroxyglutarate regulates $CD8^+$ T-lymphocyte fate," *Nature*, 540(7632): 236-241 (2016).

Van Der Windt et al., "Mitochondrial Respiratory Capacity Is A Critical Regulator Of $CD8^+$ T Cell Memory Development," *Immunity*, 36(1): 68-78 (2012).

Verdeil, "MAF drives $CD8^+$ T-cell exhaustion," *Oncoimmunology*, 5(2): e1082707 (2016).

Wang et al., "Metabolic reprogramming and metabolic dependency in T cells," *Immunol. Rev.*, 249(1): 14-26 (2012).

Warburg, "On the Origin of Cancer Cells," Science, 123(3191): 309-314 (1956).

Wherry et al., "Molecular and cellular insights into T cell exhaustion," *Nat. Rev. Immunol.*, 15(8): 486-499 (2015).

Xie et al., "Targeting lactate dehydrogenase-A inhibits tumorigenesis and tumor progression in mouse models of lung cancer and impacts tumor initiating cells," *Cell Metab.*, 19(5): 795-809 (2014).

Zeng et al., "The molecular basis of IL-21-mediated proliferation," *Blood*, 109: 4135-4142 (2007).

Zeng et al., "mTORC1 couples immune signals and metabolic programming to establish $T_{reg}$ cell function," *Nature*, 499(7459): 485-490 (2013).

Zhang et al., "Mammalian Target of Rapamycin Complex 2 Controls CD8 T Cell Memory Differentiation in a Foxo1-Dependent Manner," *Cell Reports*, 14: 1206-1217 (2016).

* cited by examiner

IL-2
IL-2+LDHi
IL-21
IL-21+LDHi

T CELLS HAVING ENHANCED ANTI-TUMOR ACTIVITY

CROSS REFERENCE TO RELATED APPLICATIONS

This patent application is a U.S. National Phase Patent Application of co-pending International Patent Application No. PCT/US2020/045100, filed Aug. 6, 2020, which claims the benefit of U.S. Provisional Patent Application No. 62/883,927, filed Aug. 7, 2019, both of which are hereby incorporated by reference herein in their entireties.

STATEMENT REGARDING FEDERALLY SPONSORED RESEARCH OR DEVELOPMENT

This invention was made with Government support under Grant Numbers HL005401 and HL005408 awarded by the NIH Intramural Program, and Grant Number BC010683 awarded by the NCI Intramural Program. The Government has certain rights in this invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 736 byte ASCII (Text) file named "758665_ST25.txt." created on Feb. 7, 2022.

BACKGROUND OF THE INVENTION

Adoptive cell therapy (ACT) using cancer-reactive T cells, i.e., CD8+ T cells, can produce positive clinical responses in some cancer patients. In connection with such treatment protocols, T cells are often cultured or expanded ex vivo in the presence of cytokines, such as, e.g., IL-2 and/or IL-21, prior to being administered to the patient.

Several obstacles to the successful use of ACT for the treatment of cancer and other conditions remain. In particular, improved methods are needed for culturing and expanding T cells ex vivo so as to obtain T cells with characteristics desirable for use in ACT.

BRIEF SUMMARY OF THE INVENTION

The invention provides a method for treating or preventing cancer in a mammal, wherein the mammal comprises cancer cells, the method comprising: (a) obtaining an isolated population of T cells; (b) preparing cultured T cells by culturing the isolated T cells ex vivo in the presence of a cytokine and a lactate dehydrogenase inhibitor; and (c) administering the cultured T cells to the mammal.

The invention also provides a modified T cell, wherein the modified T cell is a cultured T cell and wherein the cultured T cell is obtained by a method comprising culturing isolated T cells ex vivo in the presence of a cytokine and a lactate dehydrogenase inhibitor. The invention also provides a pharmaceutical composition comprising a population of such T cells.

The invention also provides a method for preparing modified T cells, the method comprising culturing isolated T cells ex vivo in the presence of a cytokine and a lactate dehydrogenase inhibitor.

BRIEF DESCRIPTION OF THE SEVERAL VIEWS OF THE DRAWING(S)

FIGS. 1A-1J collectively depict the distinctive metabolic effects of IL-2 versus IL-21.

FIG. 1A is a schematic diagram of the protocol for stimulating CD8+ T cells. Naive T cells were isolated, activated with anti-CD3+ anti-CD28 for 2 days, and then cultured with no cytokine (NC), IL-21, or IL-2 for two additional days.

FIG. 1B is a graph depicting the results of a seahorse experiment for measuring the oxygen consumption rate (OCR) for CD8+ T cells treated with no cytokine, IL-2, and IL-21, with subsequent treatment with oligomycin, FCCP, and antimycin A/rotenone, as indicated. Measurements were taken for 4-6 technical replicates. The figure is representative of 11 independent experiments. In the graph, for both the IL-21 and "no cytokine" samples, higher OCR values (pmol/min) relative to IL-2 can be seen for timepoints between 20 and 80 minutes (corresponding to treatment with oligomycin, FCCP, and antimycin A/rotenone).

Figure 1A:
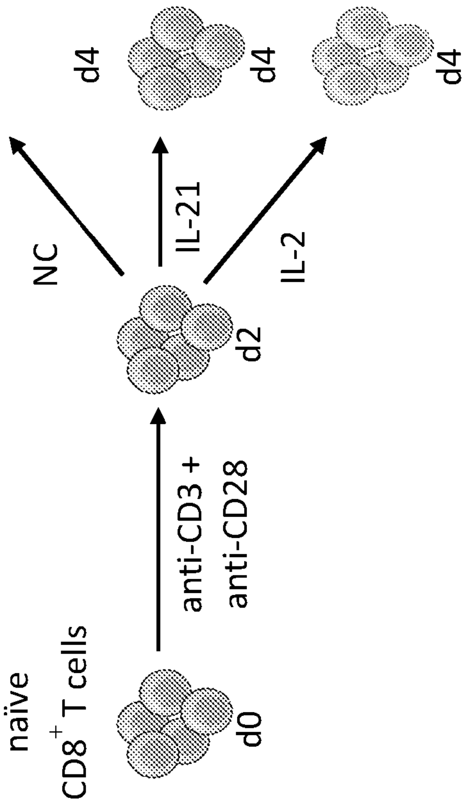
FIG. 1C is a bar graph depicting basal OCR as measured in Seahorse assays.
FIG. 1D is a bar graph depicting extracellular acidification rates ("ECAR") as measured in Seahorse assays.
FIG. 1E is a bar graph depicting spare respiratory capacity ("SRC") as measured in Seahorse assays.
Figure 1B:
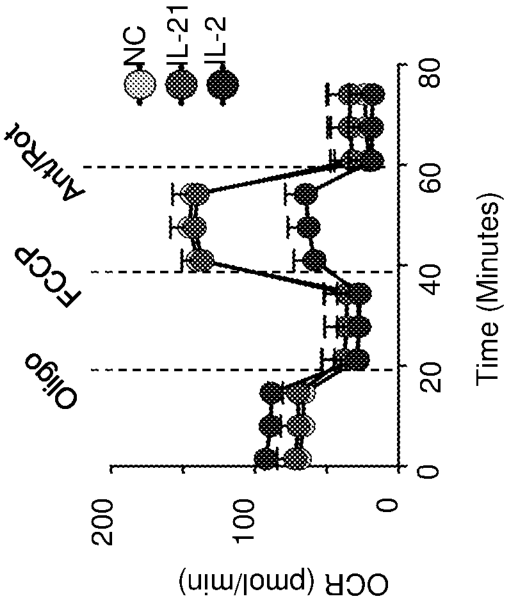
Figure 1C:
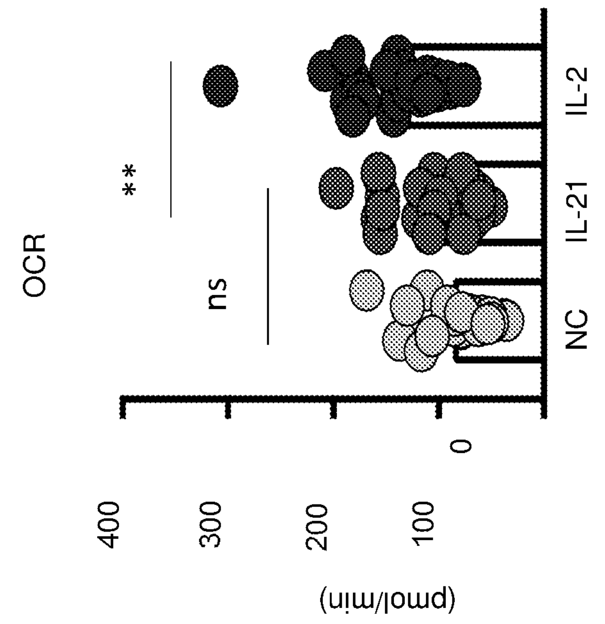
Figure 1D:
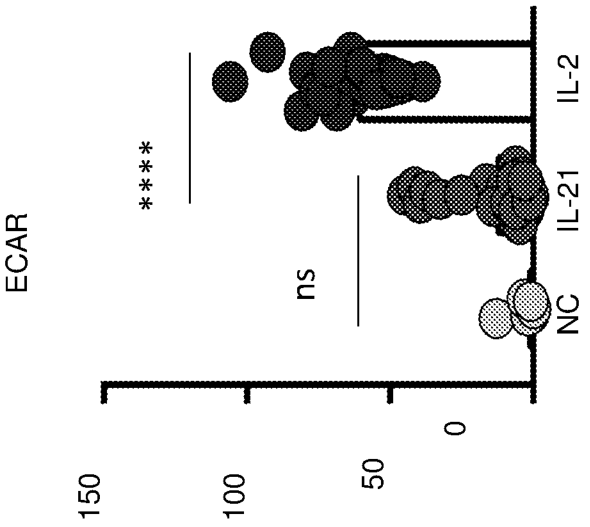
Figure 1E:
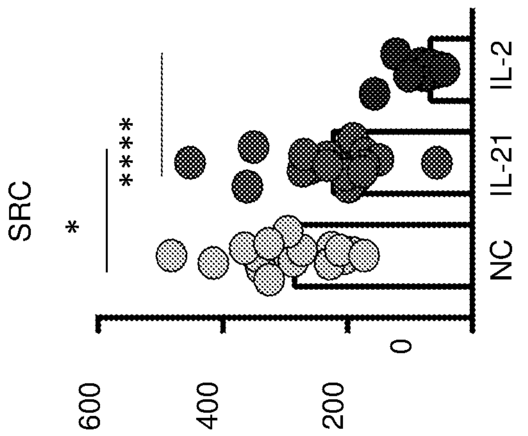
Figure 1F:
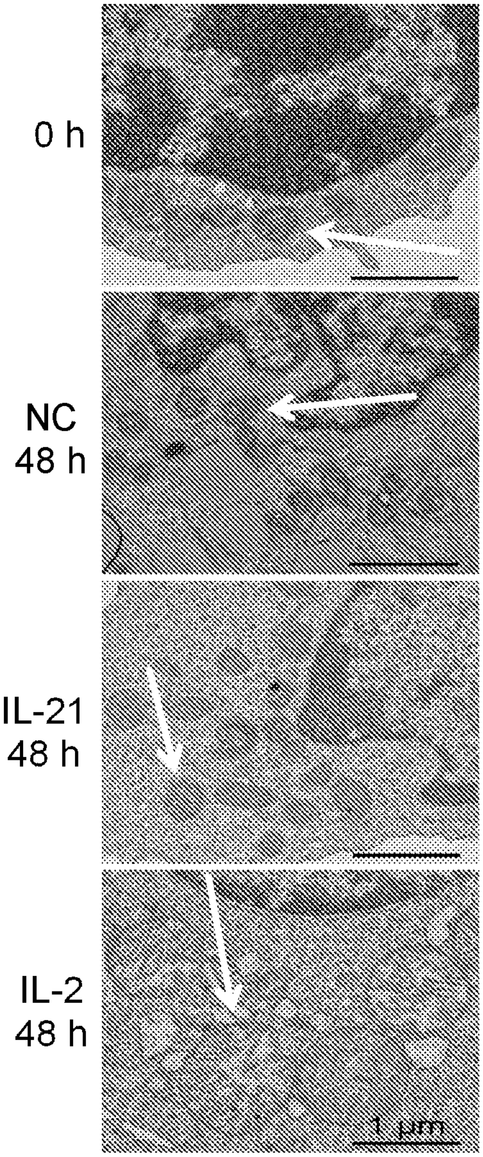

FIG. 1F provides electron micrographs representative of images from two independent experiments. Scale line=1 μm.

Figure 1G:
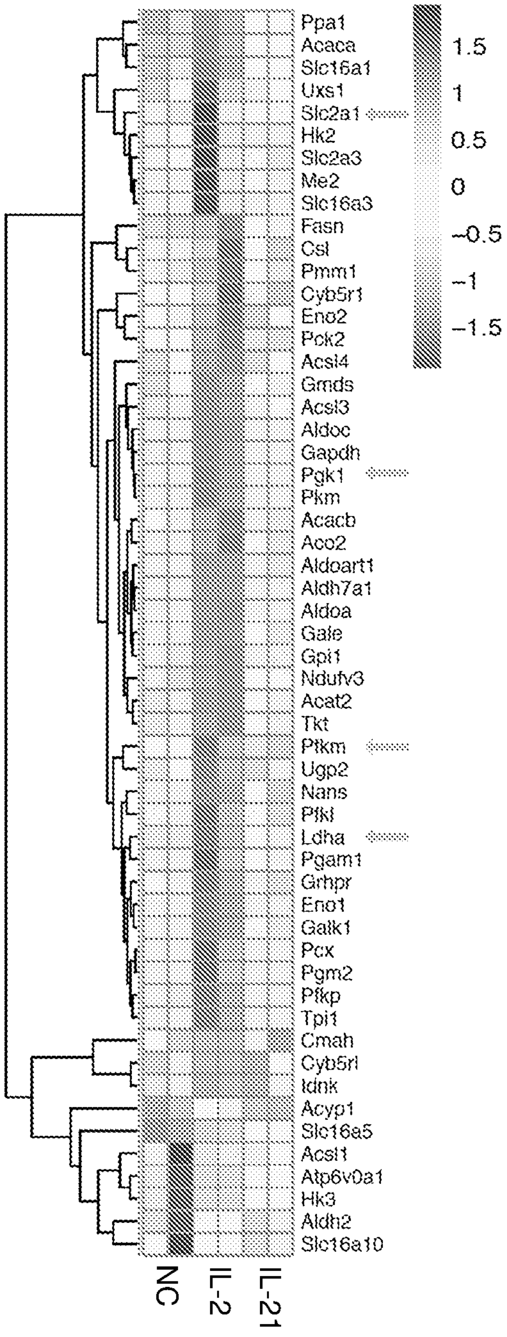

FIG. 1G is an RNA-Seq heatmap of differentially expressed metabolic genes from cells treated with NC, IL-2, or IL-21. Shown is the scale for fold-induction or repression.

Figure 1H:
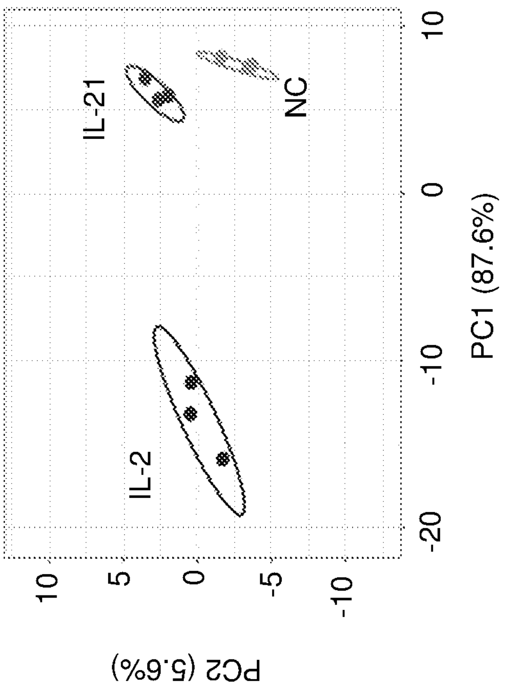

FIG. 1H is a plot depicting a principal component analysis (PCA) plot based from metabolomics data of cells treated with NC, IL-2, or IL-21.

Figure 1I:
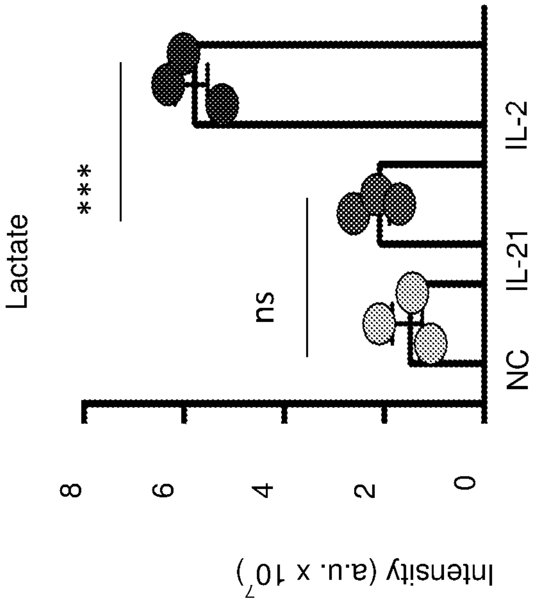

FIG. 1I is a graph depicting the results of an LC-MS-based analysis of intracellular lactate.

Figure 1J:
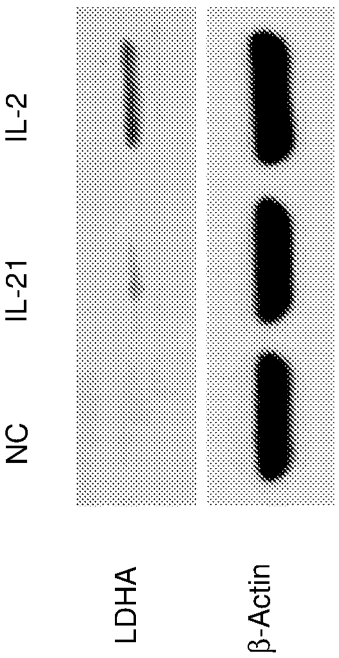

FIG. 1J is a photograph depicting protein expression of LDHA by western blotting.

FIGS. 2A-2H collectively demonstrate that LDH inhibition alters glycolytic flux and transcriptional programming.

Figure 2A:
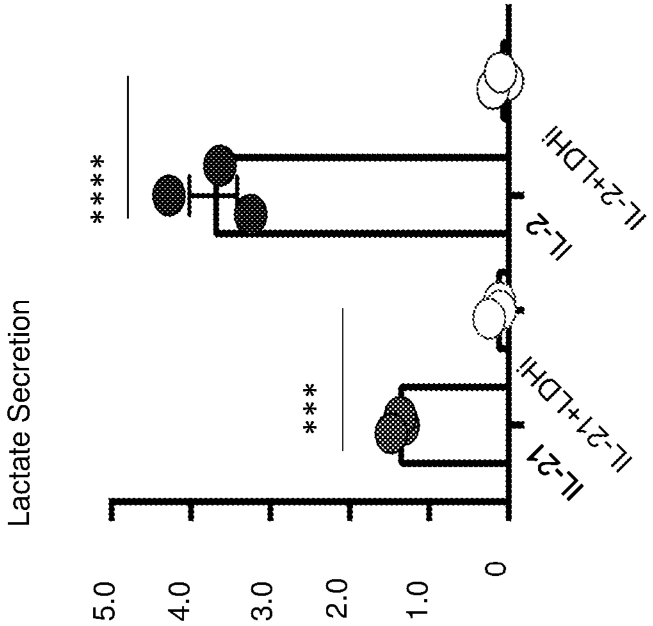

FIG. 2A is a graph depicting media measurements of lactate secretion for cells treated with IL-2 or IL-21 in the absence or presence of NCI-737 using a YSI 2900 Series Biochemical Analyzer.

Figure 2B:
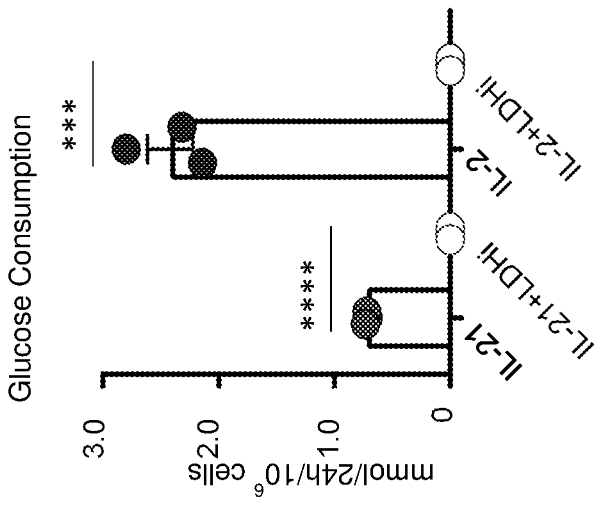

FIG. 2B is a graph depicting media measurements of glucose consumption for cells treated with IL-2 or IL-21 in the absence or presence of NCI-737 using a YSI 2900 Series Biochemical Analyzer.

Figure 2C:
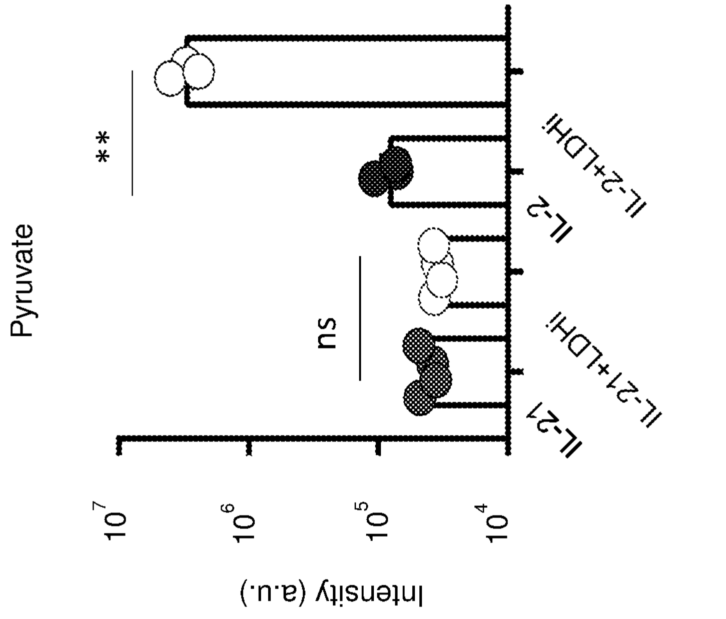

FIG. 2C is a graph depicting pyruvate levels as assessed by LC-MS for cells treated with IL-2 or IL-21 in the presence or absence of NCI-737.

Figure 2D:
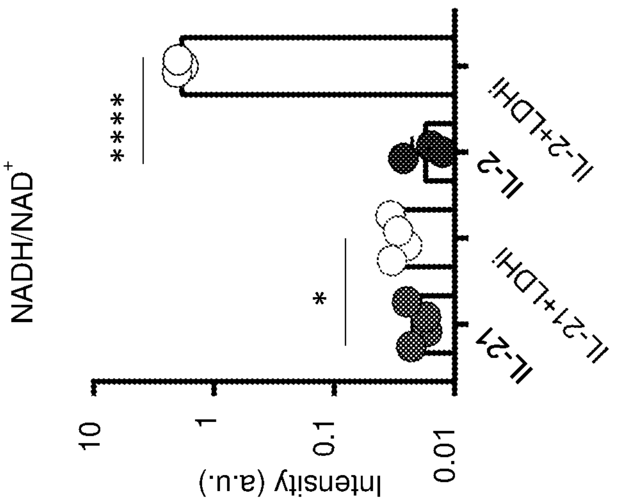

FIG. 2D is a graph depicting NADH/NAD+ levels as assessed by LC-MS for cells treated with IL-2 or IL-21 in the presence or absence of NCI-737.

Figure 2E:
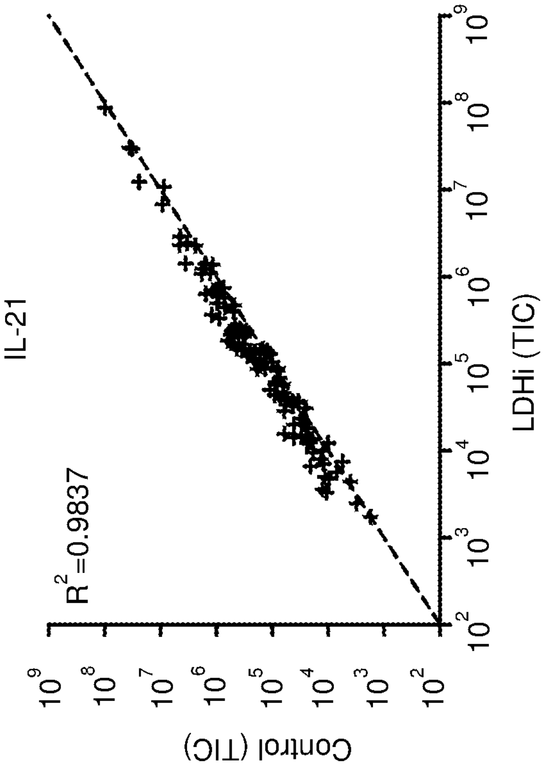

FIG. 2E is a truth plot showing correlation of intracellular metabolites for cells treated with IL-21 versus IL-21+NCI-737.

Figure 2F:
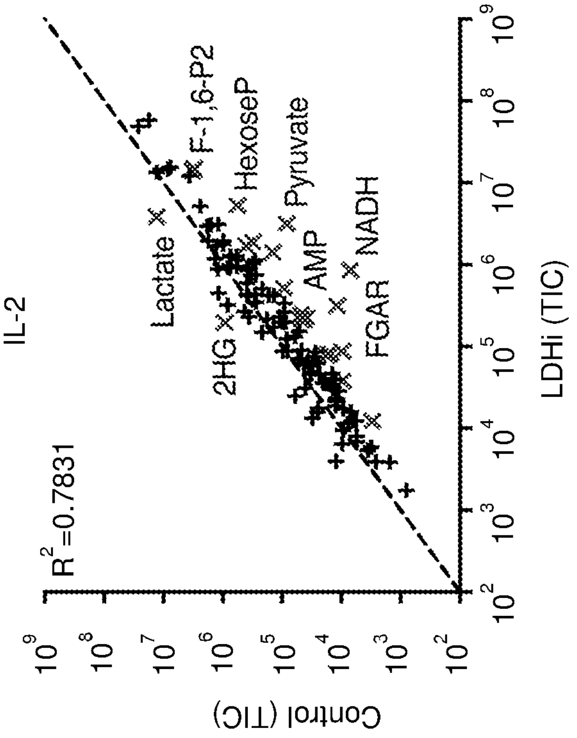

FIG. 2F is a truth plot showing correlation of intracellular metabolites for cells treated with IL-2 versus IL-2+NCI-737. The metabolites designated with an "X" had a change of greater that 4 fold.

Figure 2G:
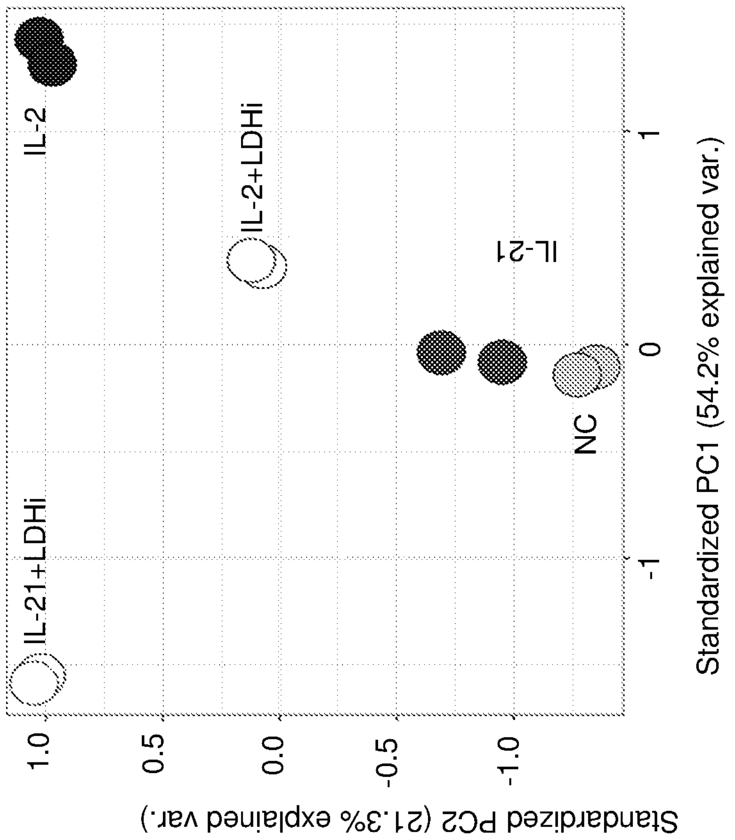

FIG. 2G is a plot depicting a principal component analysis generated from RNA-Seq data of cells treated with no cytokine ("NC"), IL-2, IL-21, IL-2+NCI-737, or IL-21+NCI-737.

Figure 2H:
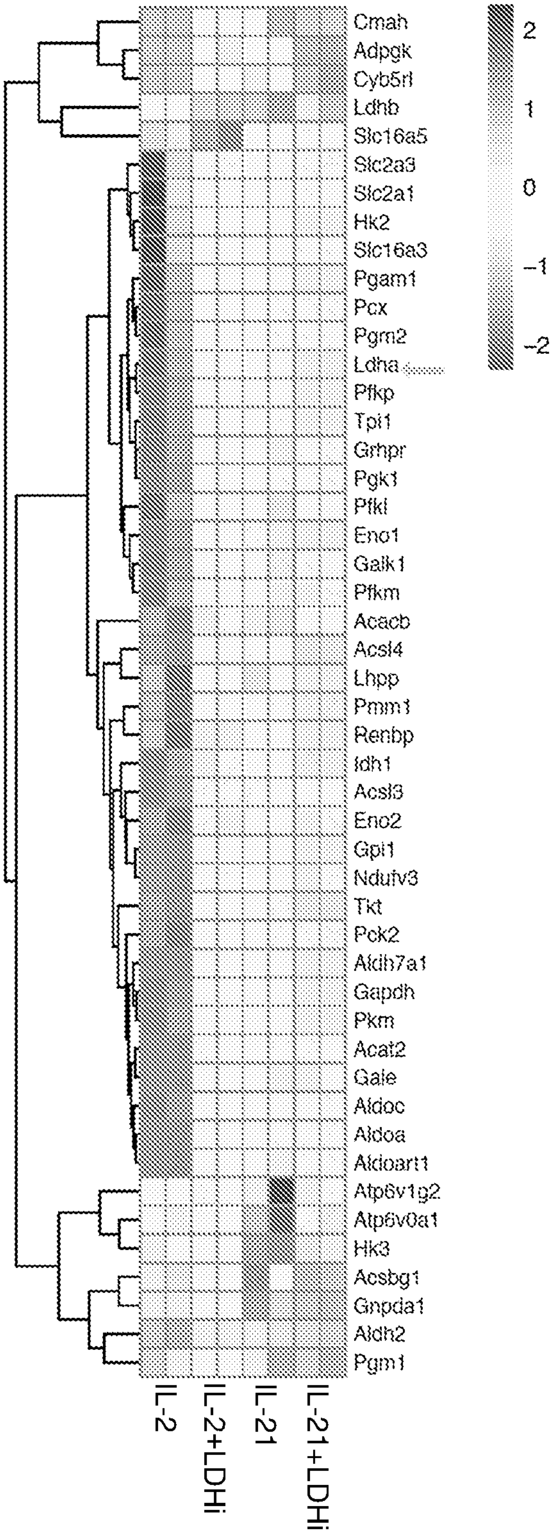

FIG. 2H is an RNA-Seq heatmap displaying differentially expressed metabolic genes between cells treated with IL-2, IL-2+NCI-737, IL-21, or IL-21+NCI-737. Each stimulation was performed in duplicate.

FIGS. 3A-3D collectively demonstrate that NCI-737 increases the contribution of glucose to the TCA cycle in IL-2 treated cells and alters mitochondrial metabolism.

Figure 3A:
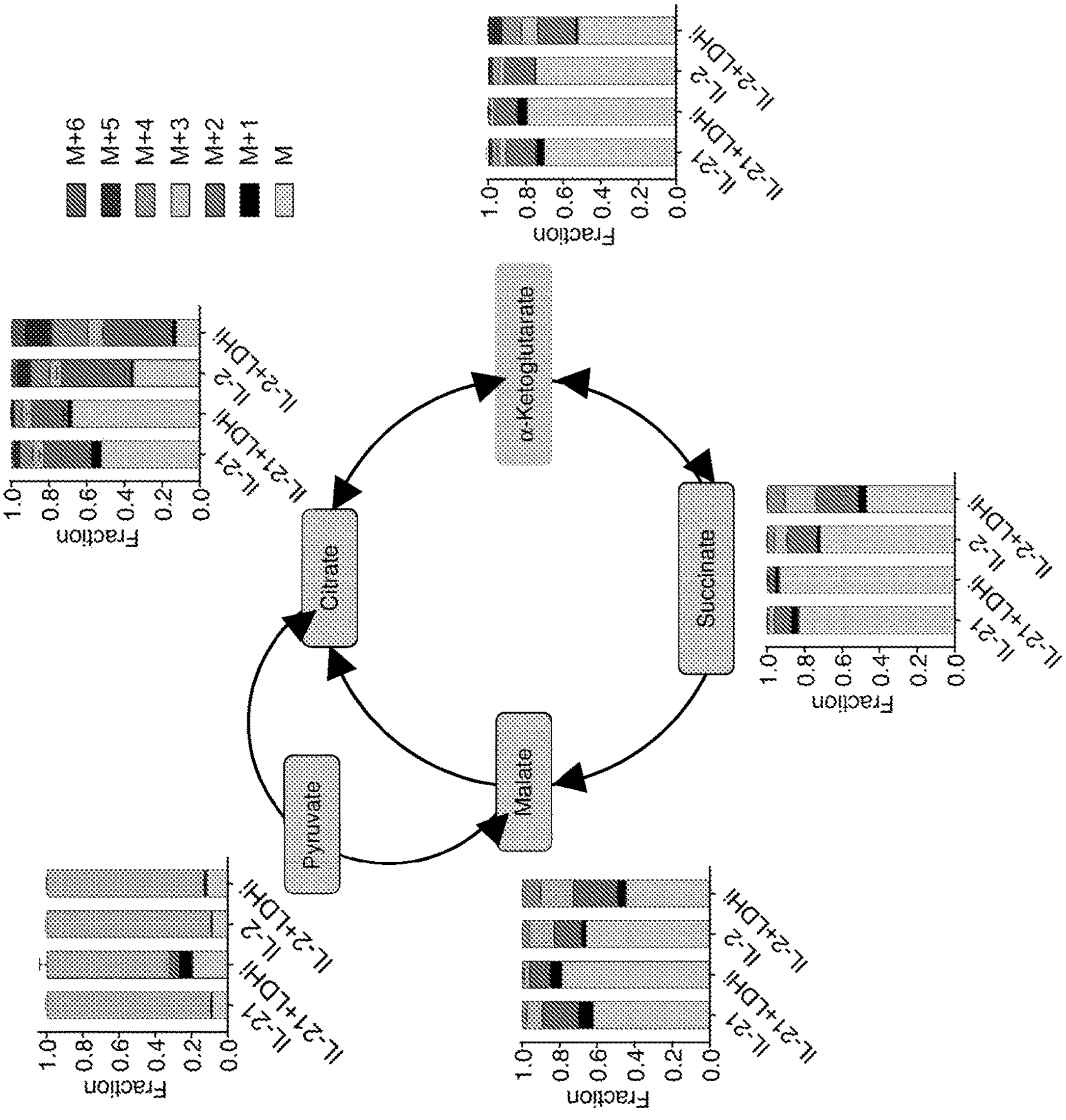

FIG. 3A is a diagram depicting the corrected 13C-labeled fraction of TCA cycle intermediates from 13C-glucose in IL-2- and IL-21-treated cells in the absence or presence of NCI-737, assessed by LC-MS.

Figure 3B:
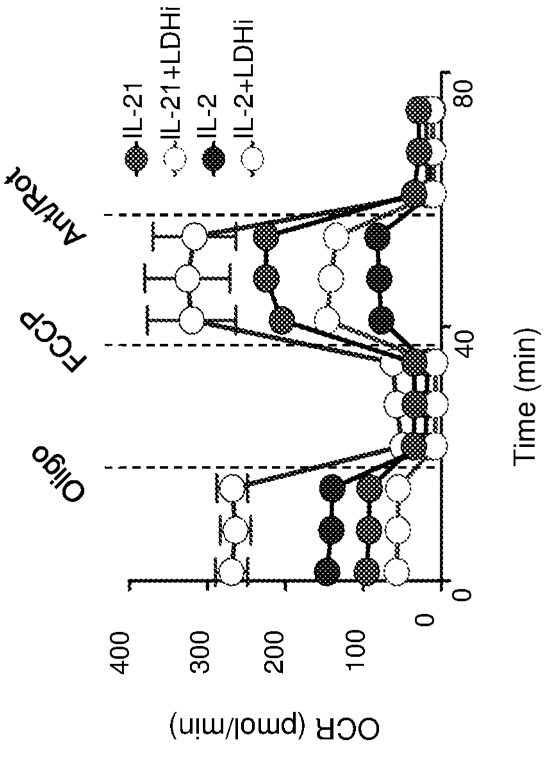

FIG. 3B is a graph depicting OCR results for cells treated with IL-2, IL-2+NCI-737, IL-21, or IL-21+NCI-737 following injection with oligomycin, FCCP, and antimycin A/rotenone. Initially IL-2+NCI-737 had the highest OCR values (in pmol/min) followed by IL-2, IL-21 and, with the lowest OCR values, IL-21+NCI-737. Upon injection with FCCP, IL-2+NCI-737 had the highest OCR value (pmol/min) followed by IL-21, IL-21+NCI-737 and, with the lowest OCR values, IL-2.

Figure 3C:
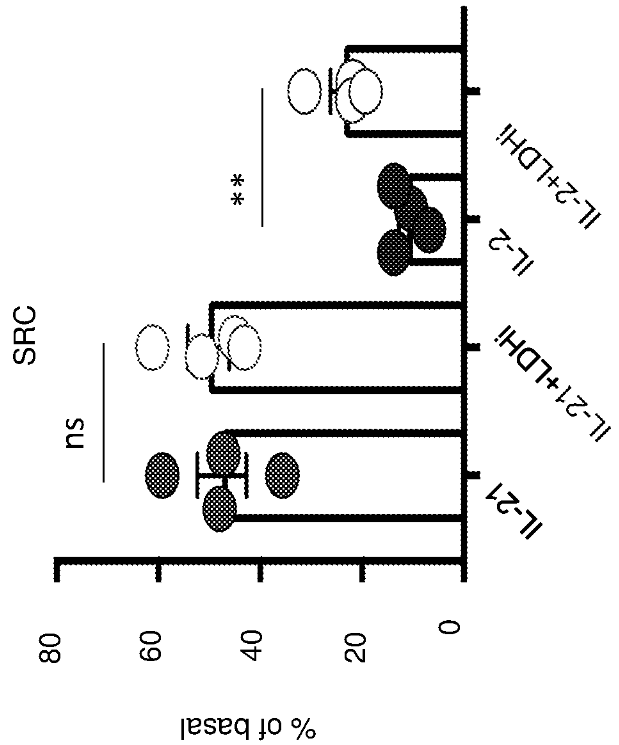

FIG. 3C is a graph depicting quantitative measurements of SRC for cells treated with IL-21, IL-21+NCI-737, IL-2, or IL-2+NCI-737.

Figure 3D:
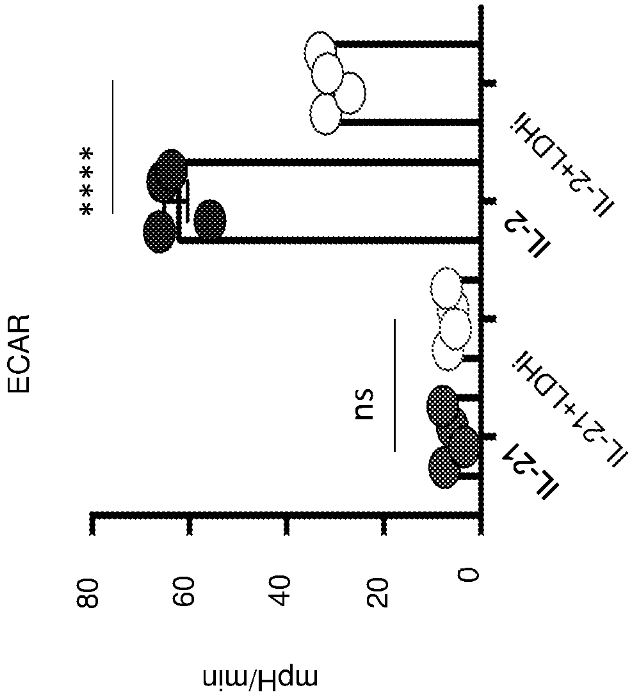

FIG. 3D is a graph depicting quantitative measurements of ECAR for cells treated with IL-21, IL-21+NCI-737, IL-2, or IL-2+NCI-737.

FIGS. 4A-4E collectively demonstrate that inhibiting LDH in vitro enhances T cell priming for effective antitumor activity in vivo.

Figure 4A:
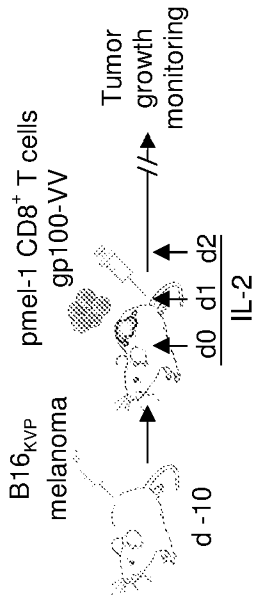

FIG. 4A is a schematic diagram of the adoptive cell transfer protocol. pmel-1+ CD8+ T cells that were cultured in the presence of anti-CD3 and anti-CD28 for 4 days, with concomitant stimulation with IL-2 or IL-21 in the absence or presence of NCI-737. Cells were then adoptively transferred into animals that that had been injected with B16 melanoma 10 days earlier. IL-2 was administered at the time of adoptive cell transfer and on each of the next two days.

Figure 4B:
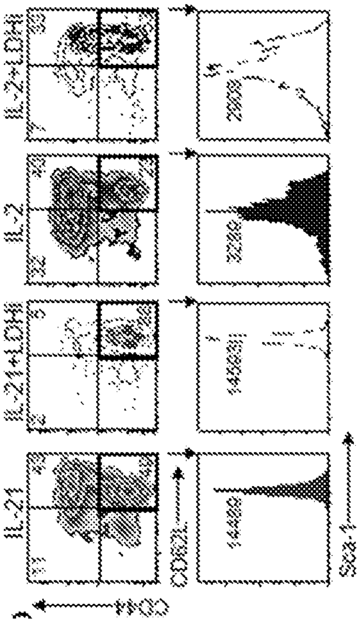

FIG. 4B depicts expression assessed on live cells (upper panels) for pmel-1 CD8 T cells were treated with IL-2 or IL-21 with and without NCI-737 and with CD44 or CD62L, and then gating was done on the CD62LhiCD4410 cells from the upper panels to assess Sca-1+ cells (histograms, lower panels).

Figure 4C:
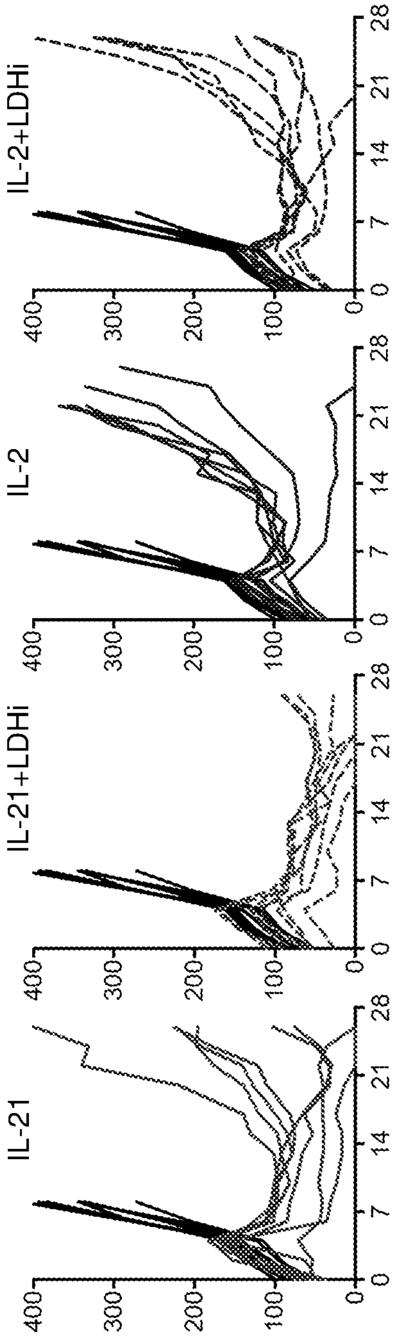

FIG. 4C is four graphs showing individual tumor size over time for each mouse in the experiment.

Figure 4D:
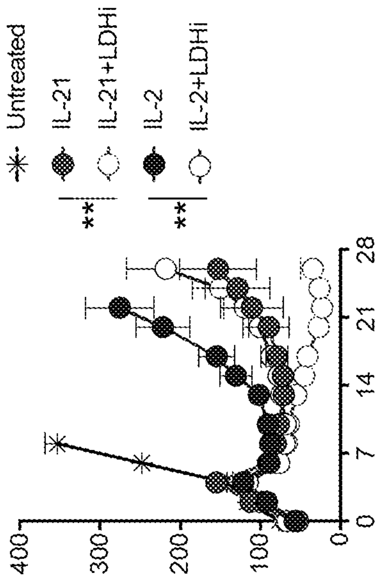

FIG. 4D is a graph depicting average tumor curves from data in FIG. 4C with untreated (indicated with the star symbol) or treated with IL-21 (solid circles), IL-21+NCI-737 (open circles), IL-2 (solid circles), or IL-2+NCI-737 (open circles). Statistics comparing tumor curves were performed using the Wilcoxon Rank Sum Test. IL-21-treated cells were more effective than IL-2-treated cells. However, in IL-2-treated cells, NCI-737 augmented the antitumor effect to the level of IL-21-treated cells, and cells generated with IL-21 and NCI-737 were the most potent.

Figure 4E:
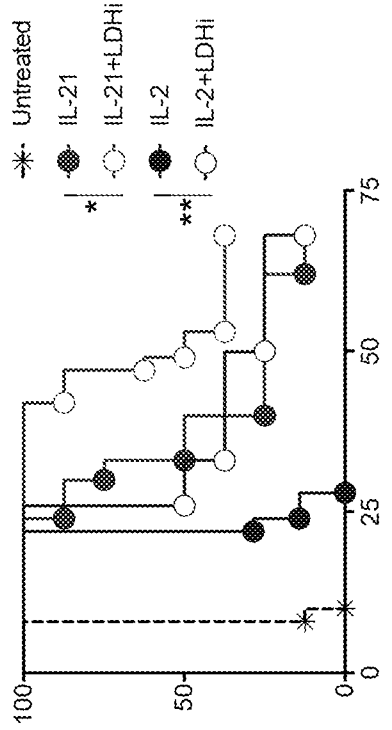

FIG. 4E is a graph depicting percent survival for each treatment group in the tumor experiment shown in FIGS. 4C and 4D with untreated (indicated with the star symbol) or treated with IL-21 (solid circles), IL-21+NCI-737 (open circles), IL-2 (solid circles), or IL-2+NCI-737 (open circles). Statistics comparing percent survival data were performed using a Logrank (Mantel-Cox) test. All tumor data are from one of two similar experiments. IL-21+NCI-737 showed the greatest survival, with IL-21 and IL-2+NCI-737 showing roughly comparable survival.

Figure 5:
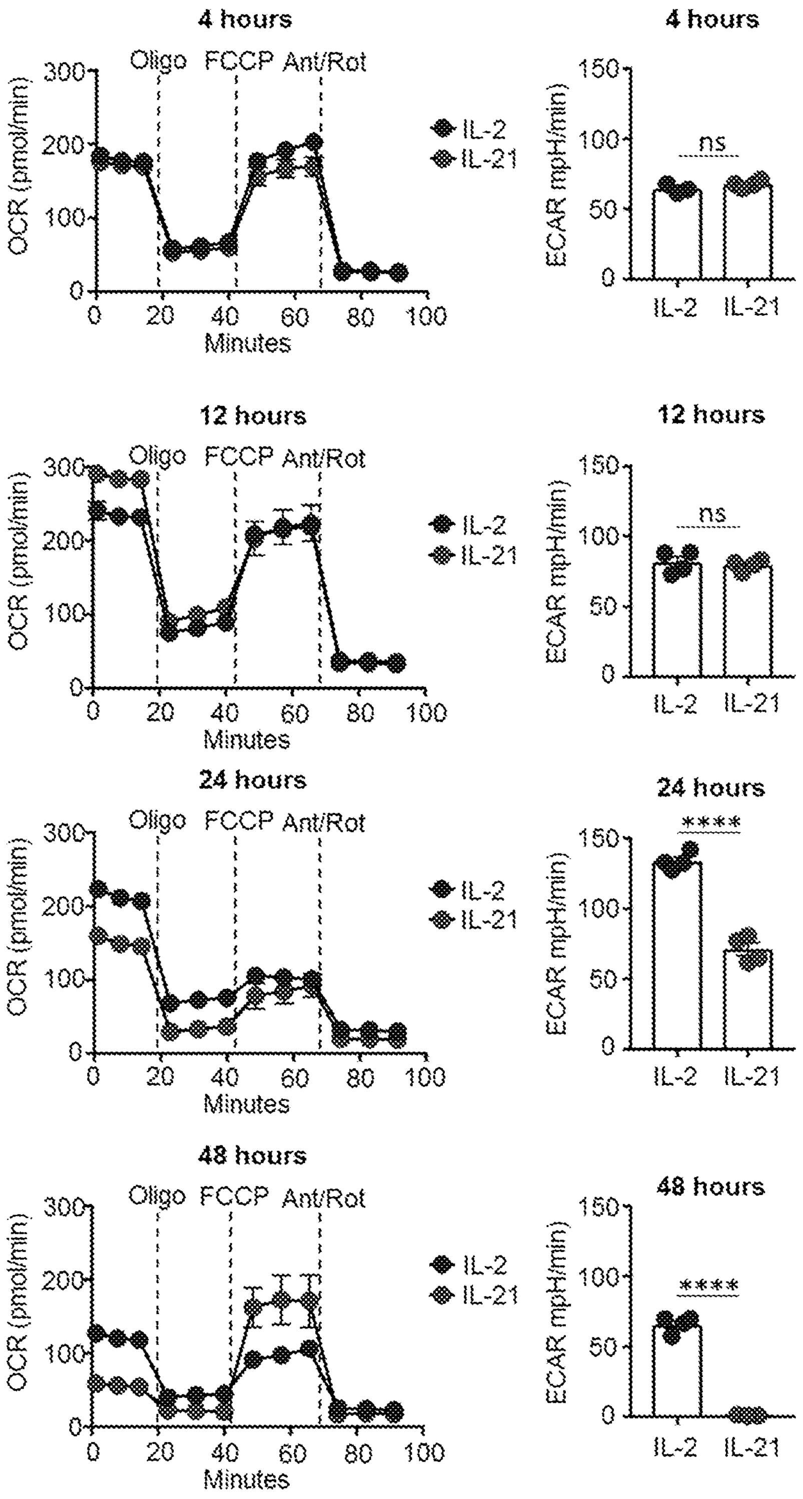

FIG. 5 is a series of graphs depicting OCR (left panels) and ECAR (right panels) induced by IL-21 and IL-2 in mouse CD8+ T cells. The OCRs are shown for CD8+ T cells treated with IL-2 or IL-21 following treatment with oligomycin, FCCP, and antimycin A/rotenone. Cells were activated with anti-CD3+anti-CD28 for 48 h before being stimulated with cytokine for 4, 12, 24, or 48 h, as indicated. Measurements at each point were taken with 4-6 technical replicates. OCR plots are on the left, and ECAR graphs are on the right. This experiment is representative of 3 independent experiments. In the 4 hour OCR plot, the OCR plots for both IL-2 and IL-21 are roughly equal at time point zero. In the 12 hour OCR plot, at time 0, the OCR value for IL-21 is approximately 300 pmol/min, and the OCR value for IL-2 is approximately 250 pmol/min. In the 24 hour OCR plot, at time 0, the OCR value for IL-21 is below 200 pmol/min and the OCR value for IL-2 is above 200 pmol/min. In the 48-hour plot, at time 0, the OCR value for IL-21 is below 100 pmol/min, and the OCR value for IL-2 is above 100 pmol/min.

Figure 6A:
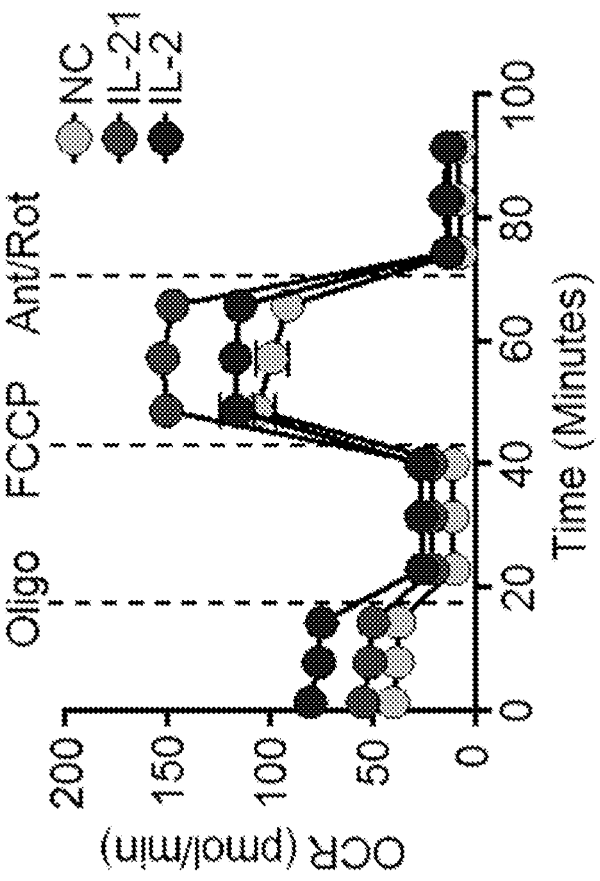
Figure 6B:
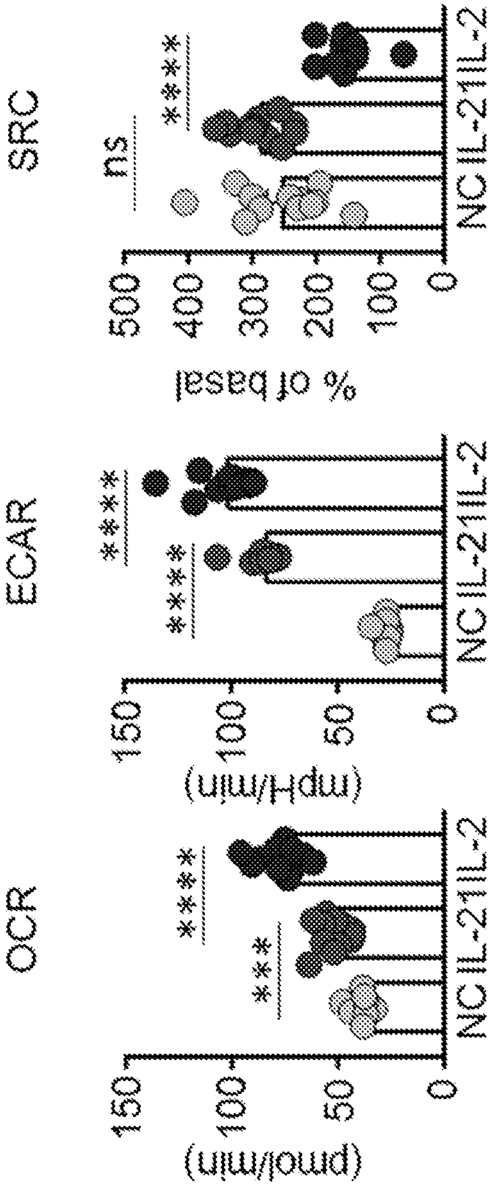

FIGS. 6A-6B collectively demonstrate the distinctive metabolic effects of IL-21 and IL-2 in human CD8+ T cells.

FIG. 6A is a graph depicting the results of seahorse experiments. The OCRs are shown for CD8+ T cells treated with no cytokine, IL-21, or IL-2, following treatment with oligomycin, FCCP, and antimycin A/rotenone. Measurements were taken for 4-6 technical replicates. At time 0, IL-2 has the highest OCR value, followed by IL-21 and the "no cytokine" cell have the lowest OCR value. After treatment with FCCP, IL-21 has the highest OCR value followed by IL-2 with the "no cytokine" cells once again having the lowest.

FIG. 6B is a series of bar graphs providing basal OCR measurements (left), basal ECAR measurements (middle), and SRC (right), as measured from Seahorse assays.

Figure 7:
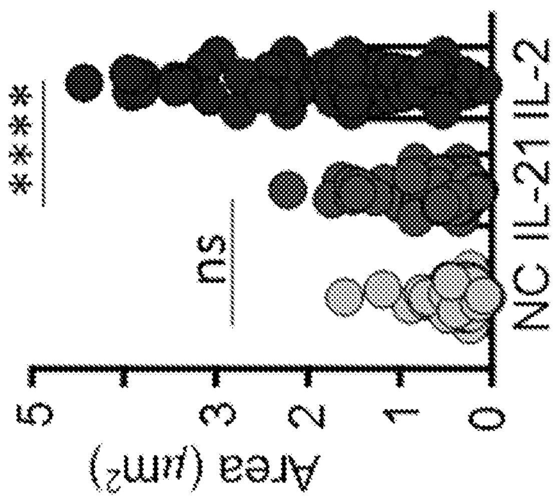

FIG. 7 is a plot depicting the calculated area of mitochondria from electron micrographs from cells treated with IL-2, IL-21, or no cytokine (NC).

Figure 8A:
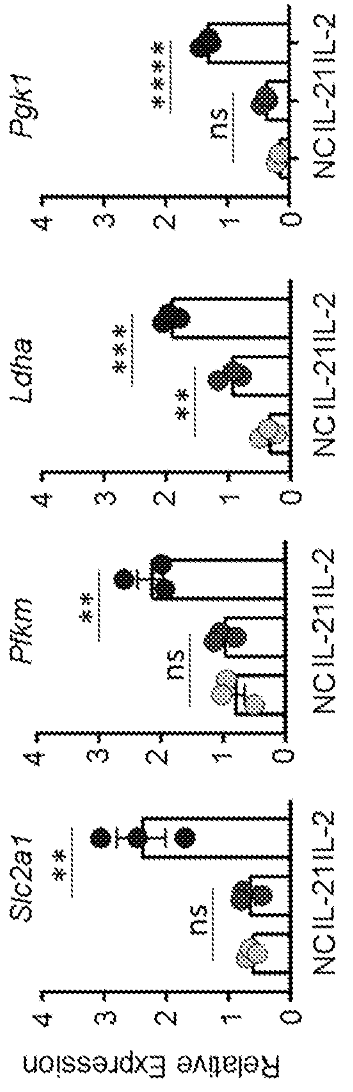
Figure 8B:
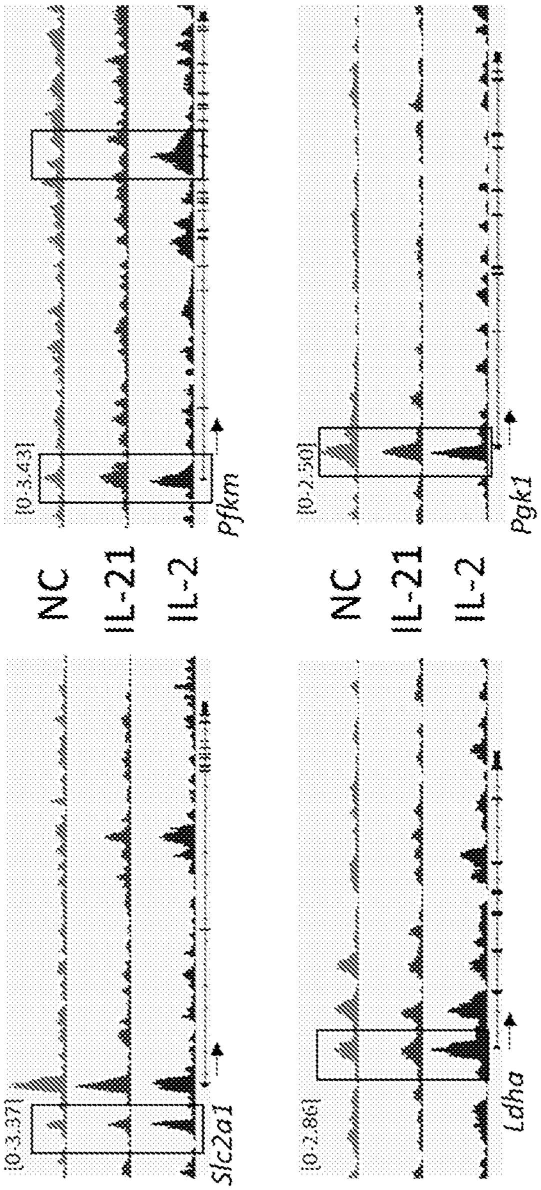

FIG. 8A-8B collectively depict IL-2-induced expression of metabolism-related genes.

FIG. 8A is a series of graphs depicting RNA expression levels by qRT-PCR of Slc2a1, Pfkm, Ldha, and Pgk1 in mouse T cells treated with no cytokine, IL-2, or IL-21. Measurements were analyzed using the ΔΔCq method of quantification.

FIG. 8B is a series of diagrams depicting ATAC-Seq analysis of Slc2a1, Pfkm, Ldha, and Pgk1 as indicated.

FIGS. 9A-9D collectively depict proliferation and viability of CD8+ T cells treated with IL-21 versus IL-2.

Figure 9A:
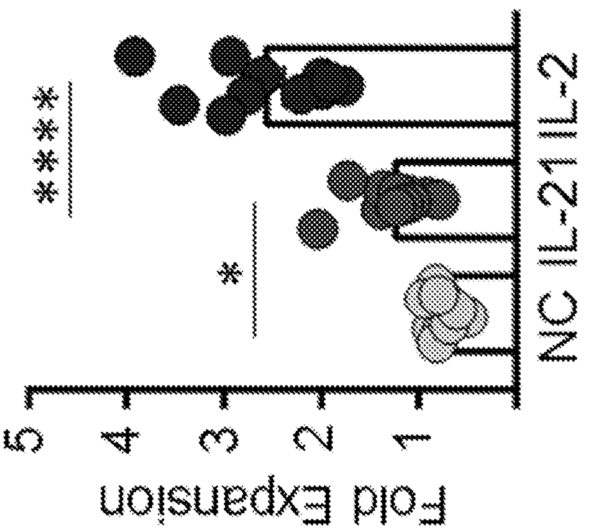

FIG. 9A is a graph depicting cellular expansion in vitro following 48 h of treatment with no cytokine, IL-21, or IL-2. Measurements were pooled from 4 independent experiments.

Figure 9B:
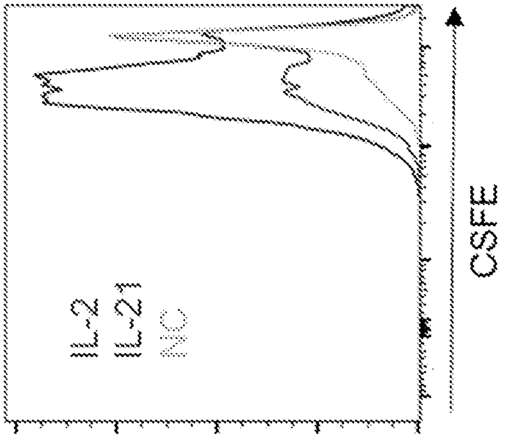

FIG. 9B is a diagram depicting flow cytometry graph of CFSE staining for activated cells treated for 48 h with no cytokine, IL-21, or IL-2. The plot with the highest peak corresponds to IL-2 and the plot with the second highest peak corresponds to "no cytokine".

Figure 9C:
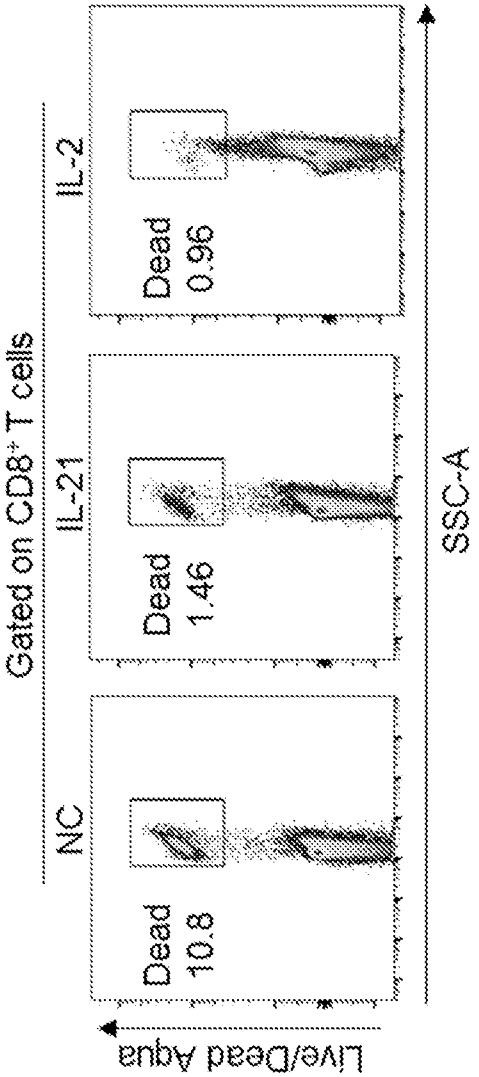

FIG. 9C is a series of plots of SSC-A versus Live/Dead Aqua flow cytometry graphs gated on CD8+ T cells. Samples are from cells stimulated with no cytokine, IL-21, or IL-2.

Figure 9D:
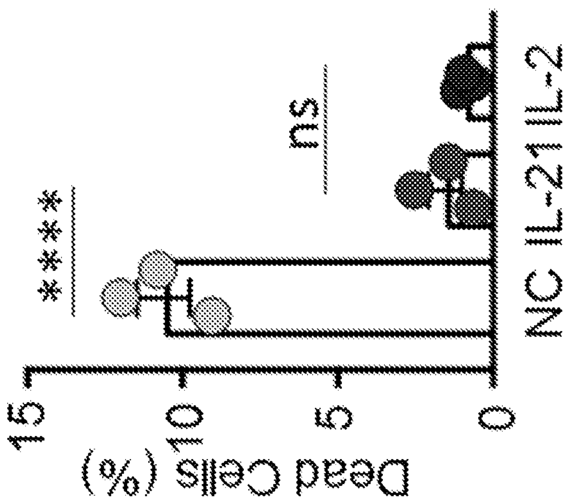

FIG. 9D is a graph depicting flow cytometry-derived percentage of dead cells following 48 h of treatment with no cytokine, IL-21, or IL-2.

FIGS. 10A-10F collectively demonstrate metabolomic repertoires in NC-, IL-2-, and IL-21-treated cells. IL-2 induces LDHA and regulates the fate of pyruvate.

Figure 10A:
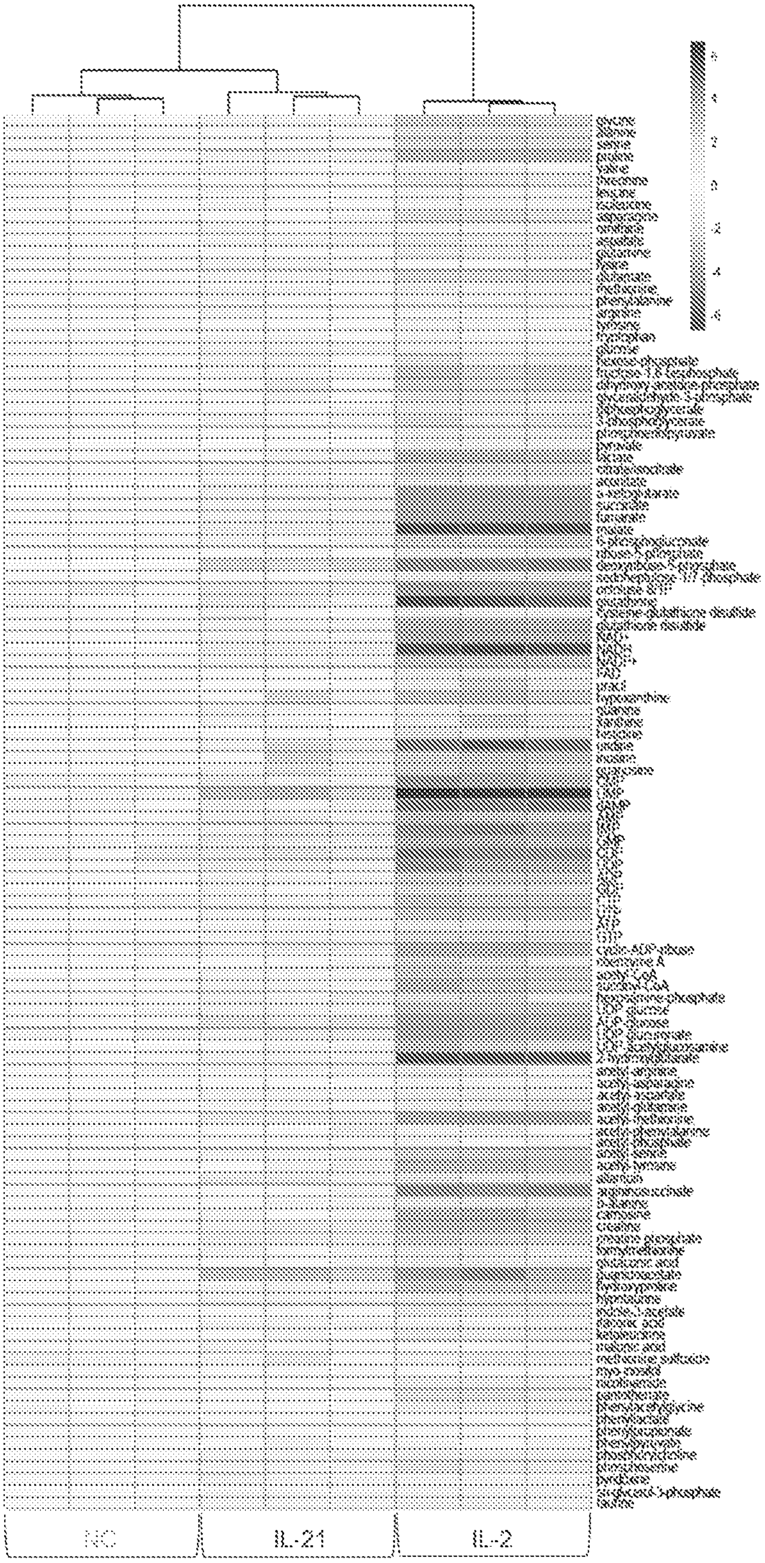

FIG. 10A is a heatmap of differential concentrations of cellular metabolites expressed as log 2FC using NC as reference (n=3).

Figure 10B:
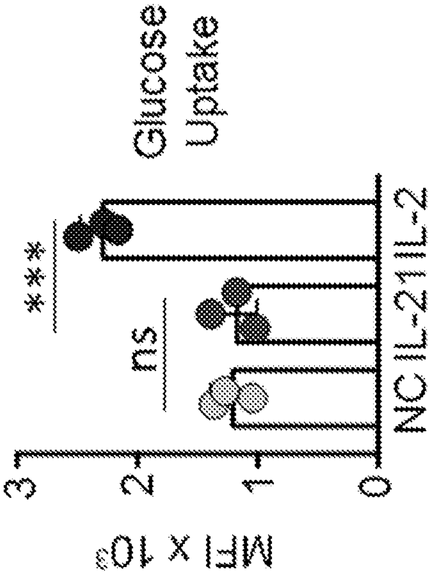

FIG. 10B is a graph depicting FACS measurement of glucose uptake in mouse T cells pre-activated with anti-CD3+ anti-CD28 for 48 h and then treated with no cytokine, IL-2, or IL-21.

Figure 10C:
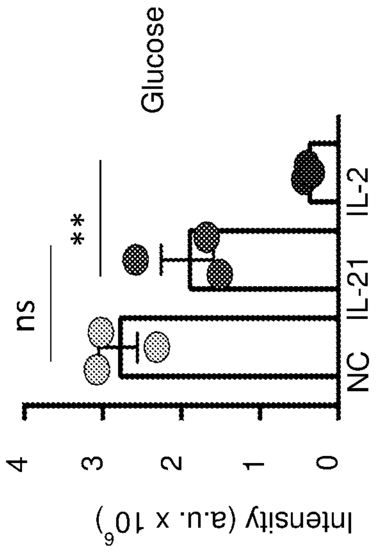

FIG. 10C is a graph depicting FACS measurement of LC-MS-based analysis of intracellular glucose in mouse T cells pre-activated with anti-CD3 and anti-CD28 for 48 h and then treated with no cytokine, IL-2, or IL-21.

Figure 10D:
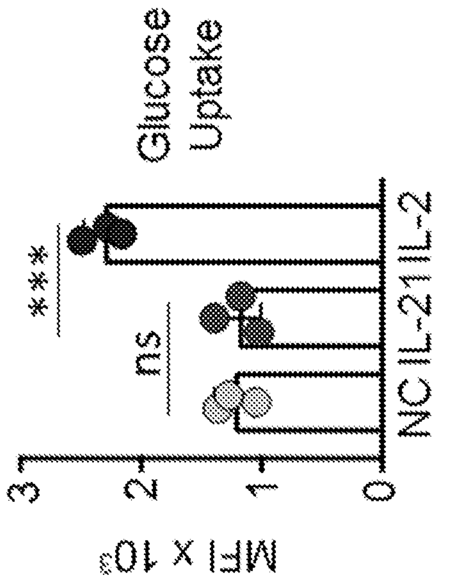

FIG. 10D is a graph depicting FACS measurement of pyruvate in mouse T cells pre-activated with anti-CD3 and anti-CD28 for 48 h and then treated with no cytokine, IL-2, or IL-21.

Figure 10E:
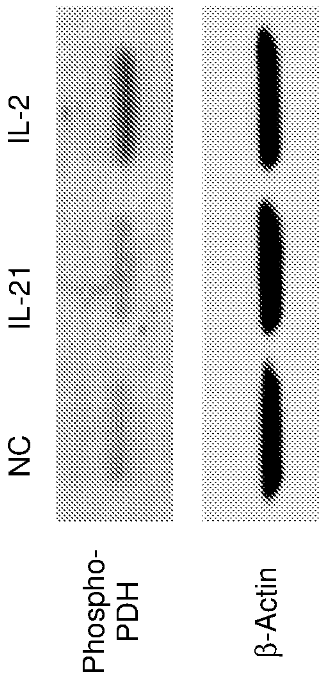

FIG. 10E is a photograph depicting the results of a Western blot of phosphorylated PDH (upper panel) and β-actin loading control (lower blot).

Figure 10F:
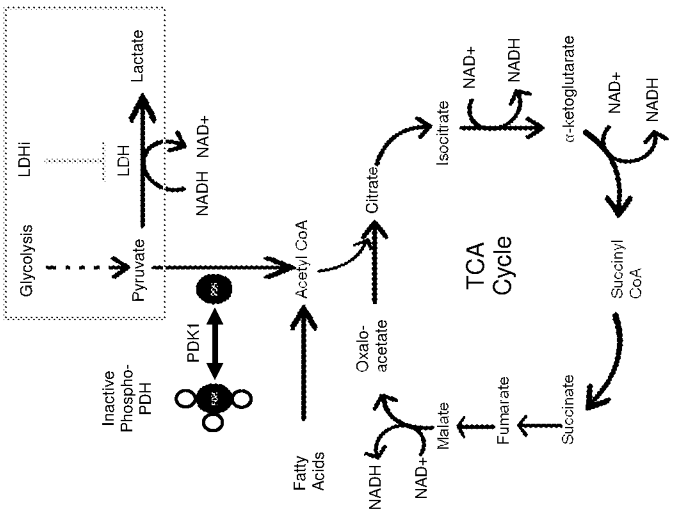

FIG. 10F is a schematic diagram of metabolic pathways and regulatory genes important for pyruvate access to the TCA cycle and fermentation. The boxed region shows the effect of NCI-737.

Figure 11A:
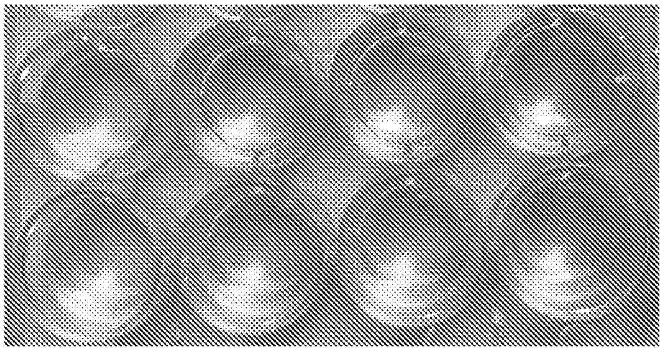
Figure 11B:
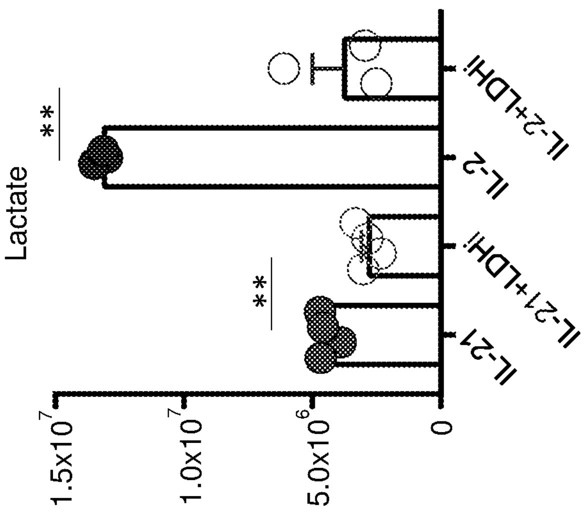
Figure 11C:
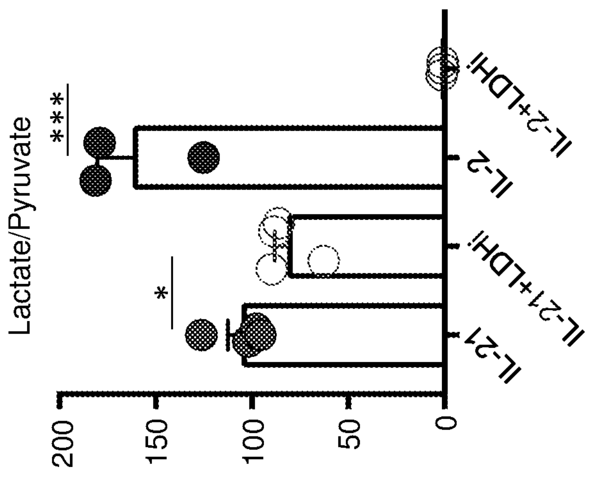

FIGS. 11A-11C collectively demonstrate increased lactate production and lactate/pyruvate ratio in IL-21 and IL-2 treated cells.

FIG. 11A is a photograph which depicts the results of an experiment demonstrating that greater acidity of CD8+ T cells treated with IL-2 is reversed by NCI-737. The photograph depicts cell media color after activated CD8+ T cells underwent 48 h stimulation with IL-2, IL-2+NCI-737, IL-21, or IL-21+NCI-737.

FIG. 11B is a graph depicting lactate level in cells treated with IL-21 and IL-2 with and without NCI-737.

FIG. 11C is a graph depicting lactate/pyruvate ratio in cells treated with IL-21 and IL-2 with and without NCI-737.

Figure 12A:
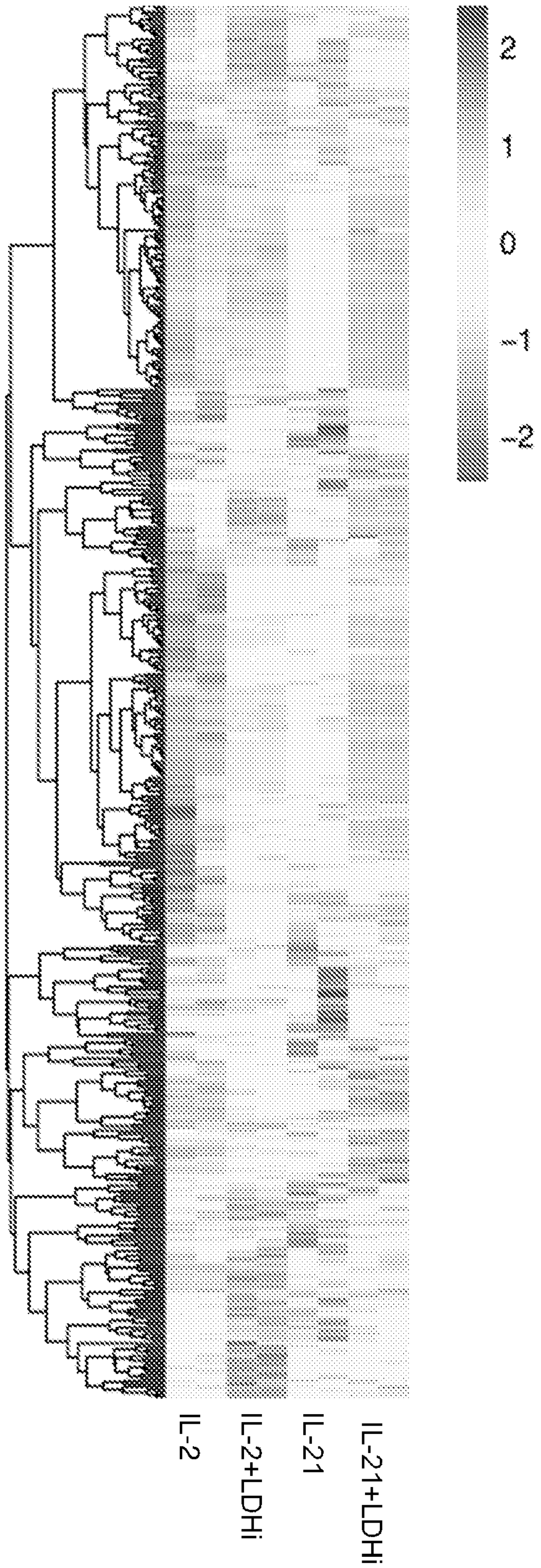
Figure 12B:
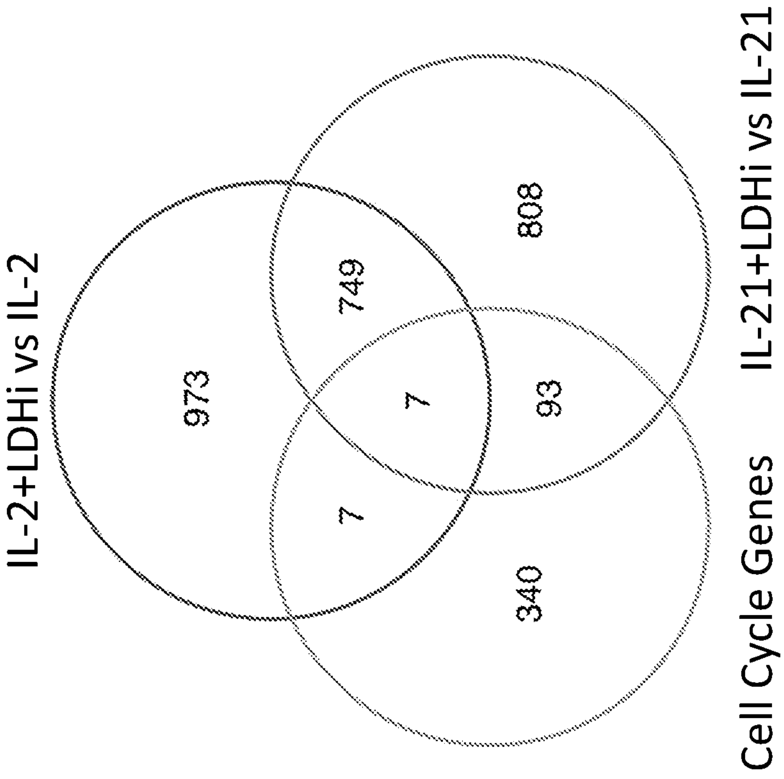

FIGS. 12A-12B collectively depict differentially expressed cell cycle genes in cells treated with IL-2, IL-2+NCI-737, IL-21, or IL-21+NCI-737.

FIG. 12A is an RNA-Seq heatmap. Color scale indicates the fold induction. Each stimulation was performed in duplicate.

FIG. 12B is a Venn diagram showing overlap of cell cycle related genes versus genes differentially expressed genes for cells treated with IL-2 versus IL-2+NCI-737 as well as IL-21 versus IL-21+NCI-737.

Figure 13A:
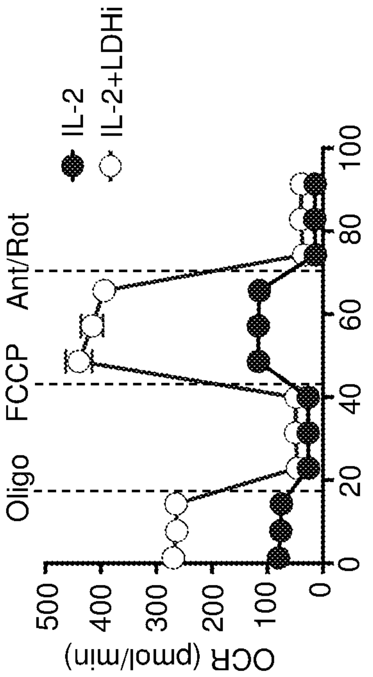
Figure 13B:
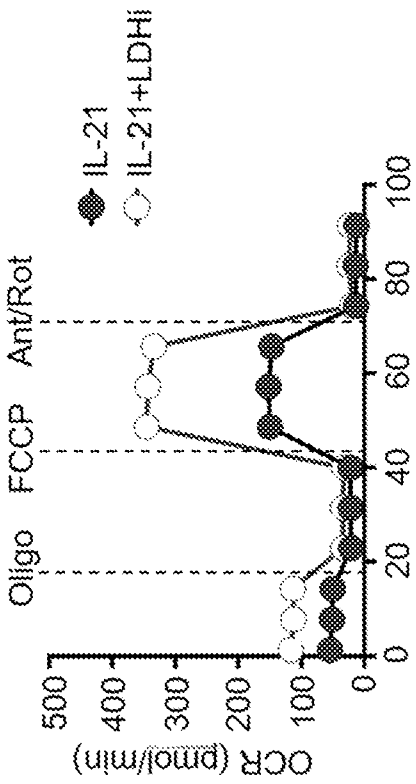

FIGS. 13A-13B collectively depict the metabolic effects of NCI-737 on IL-2- and IL-21-stimulated human CD8+ T cells.

FIG. 13A is a graph depicting OCRs for human CD8+ T cells treated with IL-2 (solid) or IL-2+NCI-737 (open).

FIG. 13B is a graph depicting OCRs for human CD8+ T cells treated with IL-21 (solid) or IL-21+NCI-737 (open).

Figure 13C:
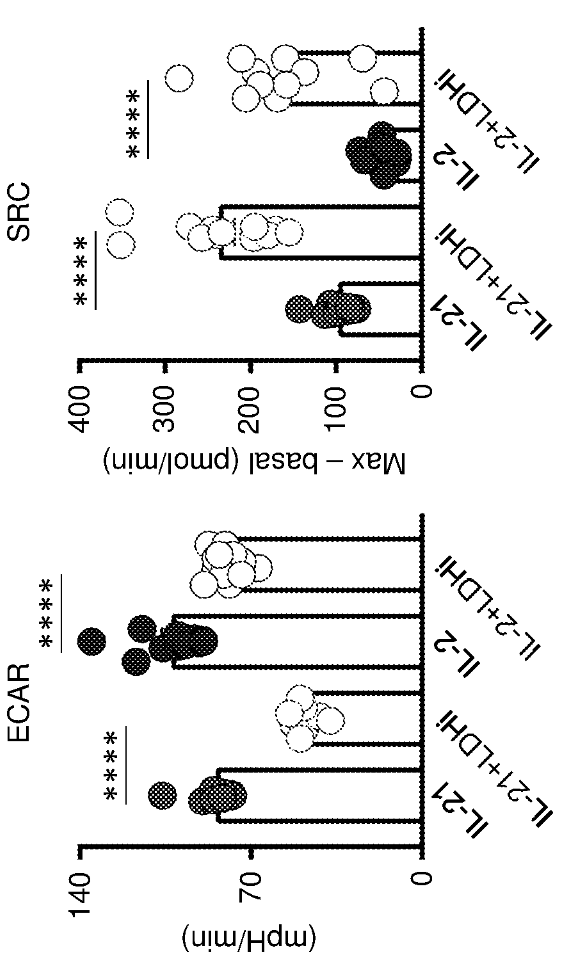

FIG. 13C is a pair of graphs depicting ECAR and SCR measurements from Seahorse graphs in FIGS. 13A and 13B.

Figure 14A:
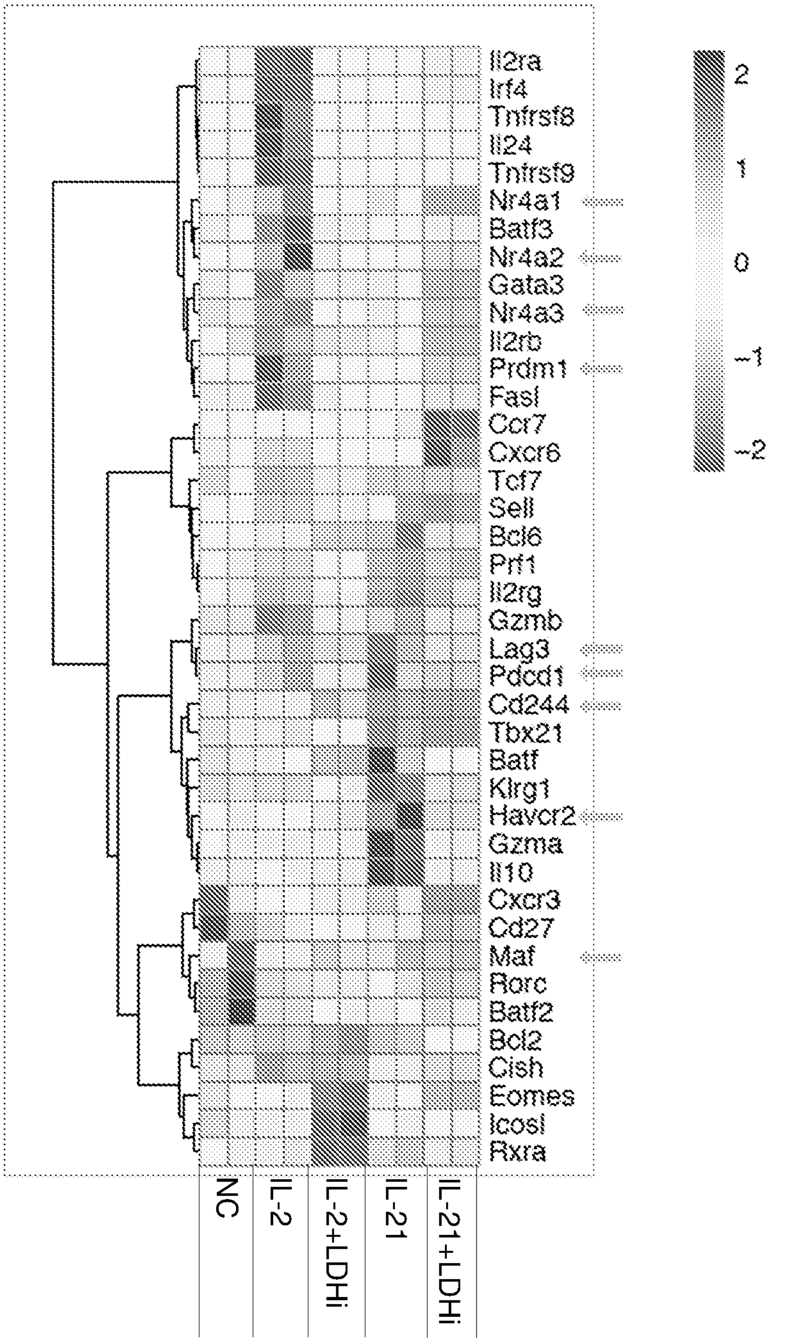
Figure 14B:
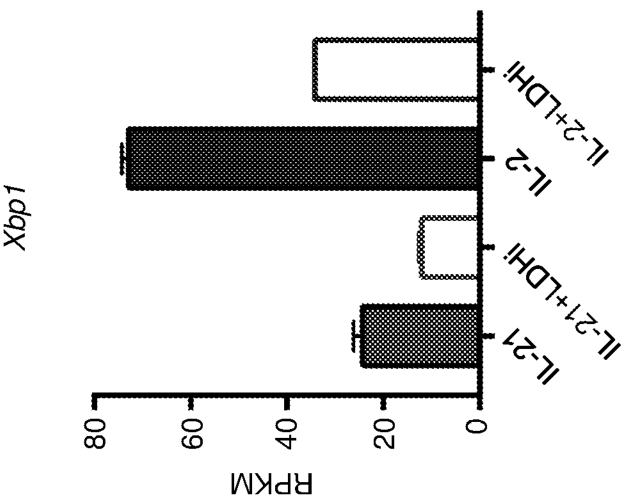

FIGS. 14A-14B collectively depict the effects of IL-2 and IL-21 without and with LDH inhibition on mRNA expression of a set of genes encompassing transcription factors, checkpoint inhibitors, costimulatory molecules, and some cytokine receptors involved in exhaustion and terminal differentiation.

FIG. 14A is an RNA-Seq heat map.

FIG. 14B is a graph depicting the effect of IL-2 and IL-21, with and without NCI-737, on expression of Xbp1.

DETAILED DESCRIPTION OF THE INVENTION

It has been discovered that T cells which have been cultured in the presence of a lactate dehydrogenase inhibitor may provide any one or more of a variety of advantages. These advantages may include, for example, greater antitumor activity as compared to control T cells, wherein the control T cells are identical to the T cells which have been cultured in the presence of a lactate dehydrogenase inhibitor except that the control T cells are not cultured in the presence of a lactate dehydrogenase inhibitor.

Lactate dehydrogenase inhibitors suitable for the invention are described in WO 2016/109559 and WO 2018/005807. In some embodiments, the lactate dehydrogenase inhibitor is defined by the structure:

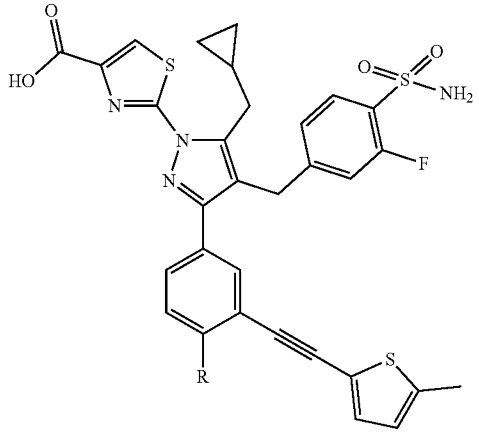

wherein R is F (Compound 390006 or NCI-006) or wherein R is H (Compound 420737 or NCI-737). Data concerning NCI-006 and NCI-737 is provided in Table 1.

TABLE 1

| NCGC ID | 390006 | 420737 | |
|---|---|---|---|
| R | F | H | |
| NSC | 787328 | 798140 | |
| MW | 650.7 | 632.7 | |
| LDH(A) - IC50 (nM) | 80 | 68 | Biochemical or Binding |
| LDA(B) - IC50 (nM) | 53 | 44 | |
| SPR $K_D$ (+NADH) (nM) | 0.0067 | 0.0063 | |
| SPR ka (+NADH) (M−1s−1) | 15000 | 16000 | |
| SPR kd (+NADH) (s−1) | <1E−06 | <1E−06 | |
| MiaPaCa Lactate OP $EC_{50}$ (nM) | 283 | 236 | Cell Biology |
| MiaPaCa CTG - $EC_{50}$ (nM) | 355 | 319 | |
| A673 Lactate OP $EC_{50}$ (nM) | 349 | 344 | |
| A673 CTG - EC50 (nM) | 305 | 221 | |
| IV 10 mg/kg AUC (h*ng/mL) | 10566 | 16530 | PK |
| PO 50 mg/kg AUC (h*mg/mL) | 31390 | 53392 | |

In some embodiments, the invention provides a modified T cell, wherein the modified T cell is a cultured T cell and wherein the cultured T cell is obtained by a method comprising culturing isolated T cells ex vivo in the presence of a cytokine and a lactate dehydrogenase inhibitor. The invention also provides a pharmaceutical composition comprising a population of such T cells. In other embodiments, the invention provides a method for preparing such modified T cells, the method comprising culturing isolated T cells ex vivo in the presence of a cytokine and a lactate dehydrogenase inhibitor. In certain embodiments, the modified T cell is a CD8+ T cell.

In some embodiments, the invention comprises harvesting and/or isolating T cells from a mammal by any suitable method known in the art. For example, T cells can be obtained from the mammal by a blood draw or a leukapheresis. In an embodiment, the T cells are harvested from the peripheral blood of the mammal. Alternatively or additionally, the T cells can be obtained from a tumor sample taken from the mammal. In this regard, the T cells may be tumor infiltrating lymphocytes (TIL). In certain embodiments, the T cells may be CD8+ T cells.

The T cells according to the invention may include any type of T cells. For example, the T cells may be a cultured T cell, e.g., a primary T cell, or a T cell from a cultured T cell line, e.g., Jurkat, SupT1, etc., or a T cell obtained from a mammal. If obtained from a mammal, the T cell can be obtained from numerous sources, including but not limited to blood, bone marrow, lymph node, the thymus, tumor, or other tissues or fluids. T cells can also be enriched for or purified. The T cell may be a human T cell. The T cell can be any type of T cell and can be of any developmental stage, including but not limited to, $CD4^+/CD8^+$ double positive T cells, $CD4^+$ T cells, e.g., $Th_1$ and $Th_2$ cells, $CD8^+$ T cells (e.g., cytotoxic T cells), $Th_9$ cells, TIL, memory T cells, naïve T cells, and the like. The T cell may be a $CD8^+$ T cell or a $CD4^+$ T cell. In certain embodiments, the T cell is a CD8+ T cell.

Production Methods

An embodiment of the invention provides a method of producing a modified T cell and/or an isolated populations comprised of such T cells. The method comprises culturing isolated T cells ex vivo in the presence of a lactate dehydrogenase inhibitor. In certain embodiments, the modified T cell is a CD8+ T cell. The lactate dehydrogenase inhibitor may be, for example, NCI-006 or Compound NCI-737. Culturing the T cells may comprise culturing the T cells in any cell culture medium comprising the lactate dehydrogenase inhibitor. Examples of cell culture media which may be useful in the inventive methods include those which are typically used for culturing T cells and may include, e.g., Roswell Park Memorial Institute (RPMI) 1640 medium, AIM V medium (ThermoFisher Scientific, Waltham, MA), or a combination thereof (e.g., Aim V:RPMI (50:50) medium). Such commercially available cell culture media (namely, "off the shelf" media) may lack lactate dehydrogenase inhibitor. The method may comprise adding the lactate dehydrogenase inhibitor to the cell culture medium which lacks the lactate dehydrogenase inhibitor for use in the inventive methods. A cell culture medium which lacks the lactate dehydrogenase inhibitor is referred to herein as "control cell culture medium" or "control cell culture media."

In an embodiment of the invention, the T cells are cultured in the presence of about 0.1 μM to about 10.0 μM of lactate dehydrogenase inhibitor. For example, the T cells may be cultured in the presence of about 0.1 μM, about 0.25 μM, about 0.5 μM, about 0.75 μM, about 1.0 μM, about 1.5 μM, about 2.0 μM, about 3.0 μM, about 3.5 μM, about 4.0 μM, about 4.5 μM, about 5.0 μM, about 5.5 μM, about 6.0 μM, about 6.5 μM, about 7.0 μM, about 7.5 μM, about 8.0 μM, about 8.5 μM, about 9.0 μM, about 9.5 μM, about 10.0 μM, or any concentration bounded by any two of the above endpoints. In an embodiment, the T cells are cultured in the presence of about 0.1 μM to about 2.0 μM of lactate dehydrogenase inhibitor. In an embodiment, the T cells are cultured in the presence of about 1.0 μM lactate dehydrogenase inhibitor.

The cell culture medium may further comprise any of a variety of additives. For example, the cell culture medium may further comprise one or more antibodies and/or one or more cytokines.

In an embodiment of the invention, the method comprises culturing the cells in the presence of a suitable amount of a lactate dehydrogenase inhibitor together with a cytokine such as, for example, interleukin-2 (IL-2), interleukin-7 (IL-7), interleukin-15 (IL-15), interleukin-12 (IL-12), or a combination of two or more of the foregoing cytokines. In an embodiment of the invention the cells are cultured in the presence of IL-2. In another embodiment, the cells are cultured in the presence of IL-21. Any suitable concentration of cytokine may be employed. For example, IL-2 may be present at a concentration of, about 100 IU/ml. As an additional example, IL-21 may be present at a concentration of, about 100 ng/ml.

While the cells may be cultured in the presence of the lactate dehydrogenase inhibitor intermittently in vitro, in an embodiment of the invention, the cells are cultured in the presence of the lactate dehydrogenase inhibitor for the entire duration of in vitro culture, including during expansion of the numbers of cells and during any introduction of a nucleic acid encoding an antigen-specific T cell receptor or chimeric antigen receptor into the cells.

In an embodiment of the invention, the method comprises expanding the number of T cells. Expansion of the numbers of cells can be accomplished by any of a number of methods as are known in the art. In an embodiment of the invention, the numbers of cells are expanded by physically contacting the cells with one or more non-specific T cell stimuli and one or more cytokines in the presence of the lactate dehydrogenase inhibitor. Examples of non-specific T cell stimuli include, but are not limited to, one or more of irradiated allogeneic feeder cells, irradiated autologous feeder cells, anti-CD3 antibodies (e.g., OKT3 antibody), anti-4-1BB antibodies, and anti-CD28 antibodies. In a preferred embodiment, the non-specific T cell stimulus may be anti-CD3 antibodies and anti-CD28 antibodies conjugated to beads. Any one or more cytokines may be used in the inventive methods. Exemplary cytokines that may be useful for expanding the numbers of cells include interleukin (IL)-2, IL-7, IL-21, and IL-15. In an embodiment of the invention, the cells are expanded in the presence of IL-2. In another embodiment, the cells expanded in the presence of IL-21. In certain embodiments, the lactate dehydrogenase inhibitor is present only during the expansion phase.

In embodiments, the cytokine is IL-2, and culturing in the presence of a lactate hydrogenase inhibitor promotes pyruvate oxidation and entry into the citric acid cycle in the cells. In embodiments, the cytokine is IL-2 and culturing in the presence of a lactate hydrogenase inhibitor restrains IL-2-driven effector differentiation and restores T-memory stem cell ("$T_{SCM}$") formation and anti-tumor efficacy.

In other embodiments the cytokine is IL-21 and culturing in presence of a lactate hydrogenase inhibitor results in increased generation of $T_{SCM}$ cells and improved anti-tumor activity.

Population of T Cells

An embodiment of the invention further provides an isolated or purified population of T cells produced by any of the inventive methods described herein. In certain embodiments, the T cells are CD8+ T cells.

The term "isolated," as used herein, means having been removed from its natural environment. The term "purified," as used herein, means having been increased in purity, wherein "purity" is a relative term, and not to be necessarily construed as absolute purity. For example, the purity can be at least about 50%, about 60%, about 70% or about 80%, or about 90% or can be about 100%.

The population of cells produced by culturing cells in the presence of the lactate dehydrogenase inhibitor according to the inventive methods can be a heterogeneous population comprising the cells described herein, in addition to at least one other cell, e.g., a cell other than a T cell, e.g., a B cell, a macrophage, a neutrophil, an erythrocyte, a hepatocyte, an endothelial cell, an epithelial cell, a muscle cell, a brain cell, etc. Alternatively, the population of cells produced by the inventive methods can be a substantially homogeneous population, in which the population comprises mainly of the cells, e.g., T cells described herein. The population also can be a clonal population of cells, in which all cells of the population are clones of a single cell, e.g., T cell. In one embodiment of the invention, the population of cells is a clonal population comprising cells, e.g., T cells comprising a recombinant expression vector encoding the antigen-specific receptor as described herein.

The inventive isolated or purified population of cells produced according to the inventive methods may be included in a composition, such as a pharmaceutical composition. In this regard, an embodiment of the invention provides a pharmaceutical composition comprising the isolated or purified population of cells described herein and a carrier.

Preferably, the carrier is a pharmaceutically acceptable carrier. With respect to pharmaceutical compositions, the carrier can be any of those conventionally used for the administration of cells. Such pharmaceutically acceptable carriers are well-known to those skilled in the art and are readily available to the public. The pharmaceutically acceptable carrier preferably has no detrimental side effects or toxicity under the conditions of use.

The choice of carrier will be determined in part by the particular method used to administer the population of cells. Accordingly, there are a variety of suitable formulations of the pharmaceutical composition of the invention. Suitable formulations may include any of those for parenteral, subcutaneous, intravenous, intramuscular, intraarterial, intrathecal, intratumoral, or interperitoneal administration. More than one route can be used to administer the population of cells, and, in certain instances, a particular route can provide a more immediate and more effective response than another route. In certain embodiments, the cells administered intravenously.

Cancer Prevention and Treatment

In other embodiments, the invention provides a method for treating or preventing cancer in a mammal, wherein the mammal comprises cancer cells, the method comprising: (a) obtaining an isolated population of T cells; (b) preparing cultured T cells by culturing the isolated T cells ex vivo in the presence of a cytokine and a lactate dehydrogenase inhibitor; and (c) administering the cultured T cells to the mammal. In certain embodiments, the T cells are CD8+ T cells.

The cancer may be any cancer, including any of acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, cholangiocarcinoma, colon cancer, esophageal cancer, cervical cancer, gastrointestinal carcinoid tumor, Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, ovarian cancer, pancreatic cancer, peritoneum, omentum, and mesentery cancer, pharynx cancer, prostate cancer, rectal cancer, renal cancer (e.g., renal cell carcinoma (RCC)), small intestine cancer, soft tissue cancer, stomach cancer, testicular cancer, thyroid cancer, ureter cancer, and urinary bladder cancer. In certain embodiments, the antigen-specific receptor has specificity for a melanoma antigen.

In an embodiment of the invention, the T cells have antigenic specificity for a cancer antigen. The term "cancer antigen," as used herein, refers to any molecule (e.g., protein, polypeptide, peptide, lipid, carbohydrate, etc.) solely or predominantly expressed or over-expressed by a tumor cell or cancer cell, such that the antigen is associated with the tumor or cancer. The cancer antigen can additionally be expressed by normal, non-tumor, or non-cancerous cells. However, in such cases, the expression of the cancer antigen by normal, non-tumor, or non-cancerous cells is not as robust as the expression by tumor or cancer cells. In this regard, the tumor or cancer cells can over-express the antigen or express the antigen at a significantly higher level, as compared to the expression of the antigen by normal, non-tumor, or non-cancerous cells. Also, the cancer antigen can additionally be expressed by cells of a different state of development or maturation. For instance, the cancer antigen can be additionally expressed by cells of the embryonic or fetal stage, which cells are not normally found in an adult host. Alternatively, the cancer antigen can be additionally expressed by stem cells or precursor cells, which cells are not normally found in an adult host.

The cancer antigen can be an antigen expressed by any cell of any cancer or tumor, including the cancers and tumors described herein. The cancer antigen may be a cancer antigen of only one type of cancer or tumor, such that the cancer antigen is associated with or characteristic of only one type of cancer or tumor. Alternatively, the cancer antigen may be a cancer antigen (e.g., may be characteristic) of more than one type of cancer or tumor. For example, the cancer antigen may be expressed by both breast and prostate cancer cells and not expressed at all by normal, non-tumor, or non-cancer cells. Cancer antigens are known in the art and include, for instance, CXorf61, mesothelin, CD19, CD22, CD276 (B7H3), gp100, MART-1, Epidermal Growth Factor Receptor Variant III (EGFRVIII), TRP-1, TRP-2, tyrosinase, NY-ESO-1 (also known as CAG-3), MAGE-1, MAGE-3, etc. In certain embodiments, the cancer antigen is gp100.

In an embodiment of the invention, the cancer antigen is a cancer neoantigen. A cancer neoantigen is an immunogenic mutated amino acid sequence which is encoded by a cancer-specific mutation. Cancer neoantigens are not expressed by normal, non-cancerous cells and may be unique to the patient. ACT with T cells which have antigenic specificity for a cancer neoantigen may provide a "personalized" therapy for the patient.

Accordingly, in an embodiment of the invention, the method may further comprise obtaining the isolated T cells by screening T cells obtained from a mammal for the T cells having antigenic specificity for the cancer neoantigen. The method may further comprise isolating the T cells having antigenic specificity for the cancer neoantigen from the cells obtained from the mammal. The isolating of the T cells may be carried out in the presence or absence of the lactate dehydrogenase inhibitor. The T cells obtained in this manner may then be cultured in the presence of the lactate dehydrogenase inhibitor as described herein with respect to other aspects of the invention. Methods of screening and isolating T cells having antigenic specificity for a cancer neoantigen are described in, for example, U.S. Patent Application Publications 2017/0218042 and 2017/0224800 and Tran et al., *Science,* 344(9): 641-645 (2014).

The terms "treat," and "prevent" as well as words stemming therefrom, as used herein, do not necessarily imply 100% or complete treatment or prevention. Rather, there are varying degrees of treatment or prevention of which a person of ordinary skill in the art recognizes as having a potential benefit or therapeutic effect. In this respect, the inventive methods can provide any amount of any level of treatment or prevention of cancer in a mammal. Furthermore, the treatment or prevention provided by the inventive method can include treatment or prevention of one or more conditions or symptoms of the disease, e.g., cancer, being treated or prevented. Also, for purposes herein, "prevention" can encompass delaying the onset or recurrence of the disease, or a symptom or condition thereof.

It is contemplated that the populations of T cells produced by culturing the T cells in the presence of the lactate dehydrogenase inhibitor can be used in methods of treating or preventing cancer in a mammal. In this regard, an embodiment of the invention provides a method of treating or preventing cancer in a mammal, comprising I administering cells to the mammal according to any of the methods described herein; (ii) administering to the mammal the cells produced according to any of the methods described herein; or (iii) administering to the mammal any of the isolated populations of cells or pharmaceutical compositions described herein; in an amount effective to treat or prevent cancer in the mammal.

In an embodiment of the invention, the method of treating or preventing cancer may comprise administering the cells or pharmaceutical composition to the mammal in an amount effective to reduce metastases in the mammal. For example, the inventive methods may reduce metastatic nodules in the mammal.

One or more additional therapeutic agents can be coadministered to the mammal. By "coadministering" is meant administering one or more additional therapeutic agents and the isolated population of cells sufficiently close in time such that the isolated population of cells can enhance the effect of one or more additional therapeutic agents, or vice versa. In this regard, the isolated population of cells can be administered first, and the one or more additional therapeutic agents can be administered second, or vice versa. Alternatively, the isolated population of cells and the one or more additional therapeutic agents can be administered simultaneously. Additional therapeutic agents that may enhance the function of the isolated population of cells may include, for example, one or more cytokines or one or more antibodies (e.g., antibodies that inhibit PD-1 function). An exemplary therapeutic agent that can be co-administered with the isolated population of cells is IL-2. Without being bound to a particular theory or mechanism, it is believed that IL-2 may enhance the therapeutic effect of the isolated population of cells, e.g., T cells.

An embodiment of the invention provides a method of administering T cells to a mammal, the method comprising culturing isolated T cells in vitro in the presence of a lactate dehydrogenase inhibitor, wherein the lactate dehydrogenase inhibitor is NCI-006 or NCI-737; and administering the T cells to the mammal after culturing the cells in the presence of the lactate dehydrogenase inhibitor. In certain embodiments, the T cells are CD8+ T cells. The culturing of the T cells in the presence of the lactate dehydrogenase inhibitor may be carried out as described herein with respect to other aspects of the invention. The isolated population of cells can be cultured ex vivo in the presence of the lactate dehydrogenase inhibitor, and then directly transferred into a mammal (preferably a human) affected by cancer. Such a cell transfer method is referred to in the art as "adoptive cell transfer" or "adoptive cell therapy" (ACT). In an embodiment of the invention, the lactate dehydrogenase inhibitor is removed (e.g., washed) from the cells prior to administering the cells to a mammal. In another embodiment of the invention, the lactate dehydrogenase inhibitor is not removed from the cells prior to administering the cells to a mammal. In an embodiment of the invention, the method comprises administering a pharmaceutical composition comprising the T cells to the mammal, wherein the pharmaceutical composition is as described herein with respect to other aspects of the invention.

Preferably, the population of cells is administered by injection, e.g., intravenously. A suitable pharmaceutically acceptable carrier for the cells for injection may include any isotonic carrier such as, for example, normal saline (about 0.90% w/v of NaCl in water, about 300 mOsm/L NaCl in water, or about 9.0 g NaCl per liter of water), NORMOSOL R electrolyte solution (Abbott, Chicago, IL), PLASMA-LYTE A (Baxter, Deerfield, IL), about 5% dextrose in water, or Ringer's lactate. In an embodiment, the pharmaceutically acceptable carrier is supplemented with human serum albumen.

For purposes of the invention, the dose, e.g., number of cells administered should be sufficient to effect, e.g., a therapeutic or prophylactic response, in the mammal over a reasonable time frame. For example, the number of cells administered should be sufficient to bind to a cancer antigen or treat or prevent cancer in a period of from about 2 hours or longer, e.g., 12 to 24 or more hours, from the time of administration. In certain embodiments, the time period could be even longer. The number of cells administered will be determined by, e.g., the efficacy of the particular population of cells to be administered and the condition of the animal (e.g., human), as well as the body weight of the animal (e.g., human) to be treated.

Many assays for determining an administered number of cells are known in the art. For purposes of the invention, an assay, which comprises comparing the extent to which target T cells are lysed or one or more cytokines such as, e.g., IFN-γ and IL-2 is secreted upon administration of a given number of such cells to a mammal among a set of mammals of which is each given a different number of the cells, e.g., T cells, could be used to determine a starting number to be administered to a mammal. The extent to which target T cells are lysed or cytokines such as, e.g., IFN-γ and IL-2 are secreted upon administration of a certain number can be assayed by methods known in the art. Secretion of cytokines such as, e.g., IL-2, may also provide an indication of the quality (e.g., phenotype and/or effectiveness) of a T cell preparation.

The number of cells administered also will be determined by the existence, nature and extent of any adverse side effects that might accompany the administration of a particular population of cells. Typically, the attending physician will decide the number of cells with which to treat each individual patient, taking into consideration a variety of factors, such as age, body weight, general health, diet, sex, route of administration, and the severity of the condition being treated. By way of example and not intending to limit the invention, the number of cells, e.g., T cells, to be administered can be about $10\times10^6$ to about $10\times10^{11}$ cells per infusion, about $10\times10^9$ cells to about $10\times10^{11}$ cells per infusion, or $10\times10^7$ to about $10\times10^9$ cells per infusion.

The T cells administered to the mammal can be allogeneic or autologous to the mammal. In "autologous" administration methods, cells are removed from a mammal, cultured in the presences of a lactate dehydrogenase inhibitor, and returned back to the same mammal. In "allogeneic" administration methods, a mammal receives cells from a genetically similar, but not identical, donor.

In the instance that the T cell(s) are autologous to the mammal, the mammal can be immunologically naïve, immunized, diseased, or in another condition prior to isolation of the cell(s) from the mammal. In some instances, it is preferable for the method to comprise immunizing the mammal with an antigen of the cancer prior to isolating the T cell(s) from the mammal, culturing the cells, and the administering of the T cell(s) or composition thereof. As discussed herein, immunization of the mammal with the antigen of the cancer will allow a population of T cells having an endogenous TCR reactive with the cancer antigen to increase in numbers, which will increase the likelihood that a T cell obtained for culturing in the presence of the lactate dehydrogenase inhibitor will have a desired antigen-specific TCR.

Unless stated otherwise, as used herein, the term "mammal" refers to any mammal including, but not limited to, mammals of the order Logomorpha, such as rabbits; the order Carnivora, including Felines (cats) and Canines (dogs); the order Artiodactyla, including Bovines (cows) and Swines (pigs); or of the order Perssodactyla, including Equines (horses). It is preferred that the mammals are non-human primates, e.g., of the order Primates, Ceboids, or Simoids (monkeys) or of the order Anthropoids (humans and apes). In some embodiments, the mammal may be a mammal of the order Rodentia, such as mice and hamsters. In other embodiments, the mammal is not a mouse. In still other embodiments, the mammal is a non-human primate or a human. In one embodiment, the mammal is the human.

In some embodiments, the mammal from which a cell is isolated is immunized with an antigen of, or specific for, a cancer. The mammal may be immunized prior to obtaining the cell from the mammal. In this way, the isolated cells can include T cells induced to have specificity for the cancer to be treated, or can include a higher proportion of cells specific for the cancer.

EMBODIMENTS

1. A method for treating or preventing cancer in a mammal, wherein the mammal comprises cancer cells, the method comprising:
   (a) obtaining an isolated population of T cells;
   (b) preparing cultured T cells by culturing the isolated T cells ex vivo in the presence of a cytokine and a lactate dehydrogenase inhibitor; and
   (c) administering the cultured T cells to the mammal.
2. The method of embodiment 1, wherein the lactate dehydrogenase inhibitor is defined by the structure:

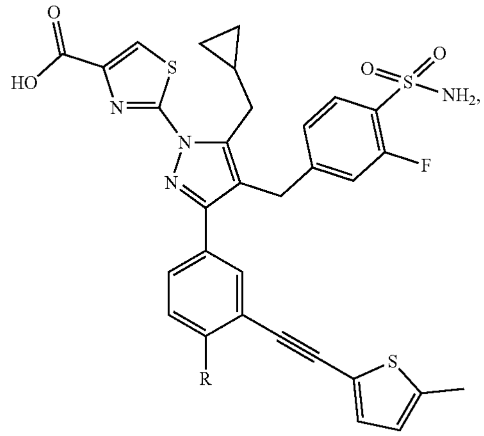

wherein R is F or H.

3. The method of embodiment 2 wherein R is F.
4. The method of embodiment 2 wherein R is H.
5. The method of any one of embodiments 1-4, wherein the cytokine is IL-2.
6. The method of any one of embodiments 1-4, wherein the cytokine is IL-21.
7. The method of any one of embodiments 1-6, wherein the T cells are CD8+ T cells.
8. The method of any one of embodiments 1-7, wherein the isolated population of T cells are obtained by harvesting the CD8+ T cells from the mammal.
9. The method of embodiment 8, wherein the T cells are harvested from the peripheral blood of the mammal.
10. The method of embodiment 8, wherein the mammal comprises a tumor and the T cells are harvested from a tumor sample taken from the mammal.
11. The method of embodiment 8, wherein the T cells are splenic.
12. The method of any one of embodiments 1-11, wherein the cancer is melanoma.
13. The method of any one of embodiments 1-12, wherein the T cells recognize an antigen present in the cancer cells.
14. The method of embodiment 13, wherein the antigen is gp100.
15. The method of any one of embodiments 1-14, wherein the cultured T cells are administered intravenously to the mammal.
16. The method of any one of embodiments 1-15, wherein the culturing of the T cells is further in the presence of one or more antibodies selected from the group consisting of an anti-CD3 antibody and an anti-CD-28 antibody.
17. The method of any one of embodiments 1-16, wherein the method further comprises administering IL-2 to the mammal after administering the cultured T cells to the mammal.
18. The method of any one of embodiments 1-17, wherein the mammal is human.
19. The method of any one of embodiments 1-18, wherein the cultured T cells are autologous to the mammal.
20. The method of any one of embodiments 1-18, wherein the cultured T cells are allogeneic to the mammal.
21. The method of any one of embodiments 1-20, wherein the method comprises expanding the number of cells in the presence of a lactate dehydrogenase inhibitor.

22. The method of any one of embodiments 1-21, wherein the method comprises administering the cultured T cells to the mammal in an amount sufficient to reduce the number of cancer cells in the mammal or to reduce metastasis of the cancer cells in the mammal.
23. The method of any one of embodiments 1-22, wherein culturing the isolated T cells in the presence of the lactate dehydrogenase inhibitor increases anti-tumor activity in the cultured T cells as compared to control cells, wherein the control cells are identical to the cultured T cells except that the control cells are not cultured in the presence of the lactate dehydrogenase inhibitor.
24. A modified T cell, wherein the modified T cell is a cultured T cell and wherein the cultured T cell is obtained by a method comprising culturing isolated T cells ex vivo in the presence of a cytokine and a lactate dehydrogenase inhibitor.
25. The modified T cell of embodiment 24, wherein the lactate dehydrogenase inhibitor is defined by the structure:

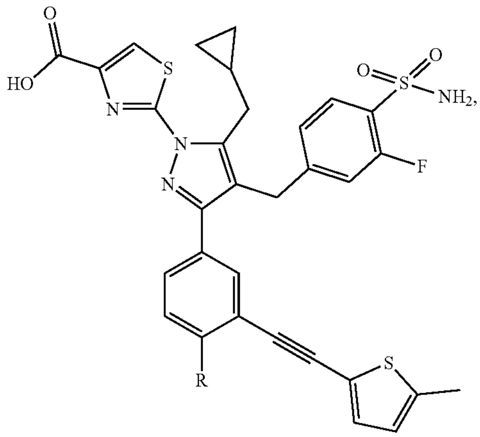

wherein R is F or H.

26. The modified T cell of embodiment 25, wherein R is F.
27. The modified T cell of embodiment 25, wherein R is H.
28. The modified T cell of any one of embodiments 24-27, wherein the cytokine is IL-2.
29. The modified T cell of any one of embodiments 24-27, wherein the cytokine is IL-21.
30. The modified T cell of any one of embodiments 24-29, wherein the T cell is a CD8+ T cell.
31. The modified T cell of any one of embodiments 24-30, wherein culturing the T cell in the presence of the lactate dehydrogenase inhibitor increases anti-tumor activity as compared to a control cell, wherein the control cell is identical to the modified T cell except that the control cell is not cultured in the presence of the lactate dehydrogenase inhibitor.
32. An isolated population of the modified T cells of any one of embodiments 24-31.
33. A pharmaceutical composition comprising a population of modified T cells of any one of embodiments 24-31, and a pharmaceutically acceptable carrier.
34. A method for preparing modified T cells, the method comprising culturing isolated T cells ex vivo in the presence of a cytokine and a lactate dehydrogenase inhibitor.
35. The method of embodiment 34, wherein the lactate dehydrogenase inhibitor is defined by the structure:

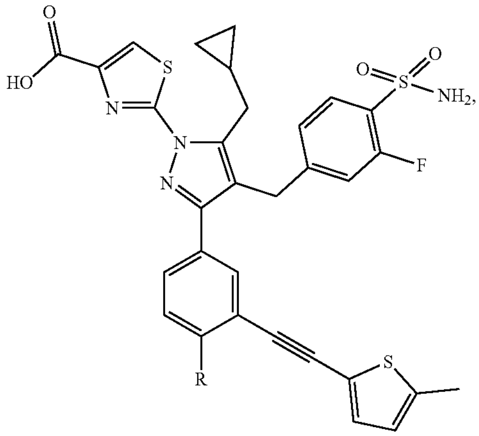

wherein R is F or H.

36. The method of embodiment 35, wherein R is F.
37. The method of embodiment 35, wherein R is H.
38. The method of any one of embodiments 34-37, wherein the cytokine is IL-2.
39. The method of any one of embodiments 34-37, wherein the cytokine is IL-21.
40. The method of any one of embodiments 34-39, wherein the T cell is a CD8+ T cell.
41. The method of any one of embodiments 34-40, wherein the culturing of the T cells is further in the presence of one or more antibodies selected from the group consisting of an anti-CD3 antibody and an anti-CD-28 antibody.
42. The method of any one of embodiments 34-41, wherein the method comprises expanding the number of cells in the presence of a lactose dehydrogenase inhibitor.
43. The method of any one of embodiments 34-42, wherein culturing the isolated T cells in the presence of the lactate dehydrogenase inhibitor increases anti-tumor activity in the modified T cells as compared to control cells, wherein the control cells are identical to the modified T cells except that the control cells are not cultured in the presence of the lactate dehydrogenase inhibitor.
44. A pharmaceutical composition comprising a population of the modified T cells prepared by the method of any one of embodiments 34-43, and a pharmaceutically acceptable carrier.
45. A composition for use in treating or preventing cancer in a mammal, wherein the mammal comprises cancer cells, wherein the composition comprises cultured T-cells and a pharmaceutically acceptable carrier, and wherein the cultured T-cells are prepared by:
(a) obtaining an isolated population of T cells; and
(b) preparing cultured T cells by culturing the isolated T cells ex vivo in the presence of a cytokine and a lactate dehydrogenase inhibitor; and wherein the composition is administered to the mammal.
46. The composition of embodiment 45, wherein the lactate dehydrogenase inhibitor is defined by the structure:

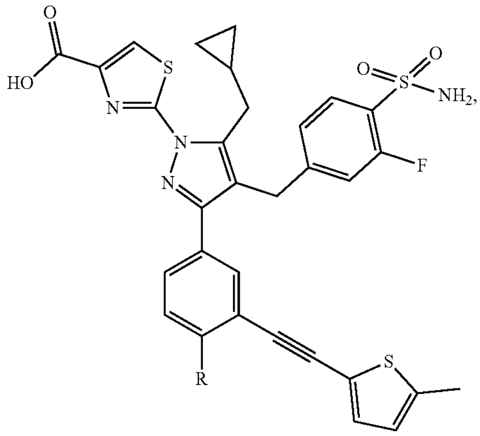

wherein R is F or H.

47. The composition of embodiment 46 wherein R is F.
48. The composition of embodiment 46 wherein R is H.
49. The composition of any one of embodiments 45-48, wherein the cytokine is IL-2.
50. The composition of any one of embodiments 45-48, wherein the cytokine is IL-21.
51. The composition of any one of embodiments 45-50, wherein the T cells are CD8+ T cells.
52. The composition of any one of embodiments 45-51, wherein the isolated population of T cells are obtained by harvesting the CD8+ T cells from the mammal.
53. The composition of embodiment 52, wherein the T cells are harvested from the peripheral blood of the mammal.
54. The composition of embodiment 52, wherein the mammal comprises a tumor and the T cells are harvested from a tumor sample taken from the mammal.
55. The composition of embodiment 52, wherein the T cells are splenic.
56. The composition of any one of embodiments 45-55, wherein the cancer is melanoma.
57. The composition of any one of embodiments 45-56, wherein the T cells recognize an antigen present in the cancer cells.
58. The composition of embodiment 57, wherein the antigen is gp100.
59. The composition of any one of embodiments 45-58, wherein the cultured T cells are administered intravenously to the mammal.
60. The composition of any one of embodiments 45-59, wherein the culturing of the T cells is further in the presence of one or more antibodies selected from the group consisting of an anti-CD3 antibody and an anti-CD-28 antibody.
61. The composition of any one of embodiments 45-60, wherein the method further comprises administering IL-2 to the mammal after administering the cultured T cells to the mammal.
62. The composition of any one of embodiments 45-61, wherein the mammal is human.
63. The composition of any one of embodiments 45-62, wherein the cultured T cells are autologous to the mammal.
64. The composition of any one of embodiments 45-62, wherein the cultured T cells are allogeneic to the mammal.
65. The composition of any one of embodiments 45-64, wherein the method comprises expanding the number of cells in the presence of a lactate dehydrogenase inhibitor.
66. The composition of any one of embodiments 45-65, wherein the method comprises administering the cultured T cells to the mammal in an amount sufficient to reduce the number of cancer cells in the mammal or to reduce metastasis of the cancer cells in the mammal.
67. The composition of any one of embodiments 45-66, wherein culturing the isolated T cells in the presence of the lactate dehydrogenase inhibitor increases anti-tumor activity in the cultured T cells as compared to control cells, wherein the control cells are identical to the cultured T cells except that the control cells are not cultured in the presence of the lactate dehydrogenase inhibitor.

EXAMPLES

The following examples further illustrate the invention but, of course, should not be construed as in any way limiting its scope.

The following materials and methods were employed in the experiments described in Examples 1-7.

Cell Preparation and Culture

Except where otherwise specified, all experiments were performed with murine splenic CD8+ T cells isolated with STEMCELL Technologies EasySep™ Mouse CD8+ T Cell Isolation Kit (catalog #19853). Following isolation, cells were resuspended at $1\times10^6$ cells/ml in T cell culture medium: RPMI 1640 medium (Thermo 11875093) containing 10% fetal bovine serum (FBS), 1× Glutamax (Life Technologies #35050-061), 1 mM sodium pyruvate, 0.1% β-mercaptoethanol, and penicillin/streptomycin. Cells were plated in 24-well tissue culture plates precoated with mouse anti-CD3 (2 μg/ml) and cultured with soluble mouse anti-CD28 (2 μg/ml) for 48 h. After incubation, cells were pooled, washed twice in media, and re-plated at 1×106 cells/ml. Cells were stimulated without cytokine or with 100 IU/ml human IL-2 or 100 ng/ml mouse IL-21. Unless otherwise specified, cells were stimulated for 48 h before being harvested. Where noted, cells were treated (1 μM) with a novel, pyrazole-based LDH inhibitor (NCI-737, herein denoted as NCI-737) that was developed under the auspices of the NCI Experimental Therapeutics Program 29. NCI-737 was added at the time of anti-CD3+ anti-CD28 treatment and replenished after cells were washed and replated in either IL-2 or IL-21, as indicated.

Western Blotting

After 3 days of stimulation with medium, IL-2, or IL-21, cells were pelleted at 1500 rpm for 5 min, washed with ice cold PBS, resuspended in radioimmunoprecipitation assay buffer, and frozen on dry ice. Frozen lysates were thawed on ice, cell debris was removed by centrifuging at 13,000 rpm for 15 min at 4° C., and supernatant was collected. Protein was quantified using the DCTM Protein Assay Kit (Bio-Rad #5000111) and 20 μg of supernatant protein was loaded into the wells of a NuPAGE™ 4-12% Bis-Tris Gel (Invitrogen #NP0335BOX) and electrophoresed at 100 V in NuPAGE MOPS SDS Running Buffer (Life Technologies #1908733). Proteins were transferred onto a 0.45 μm polyvinylidene difluoride membrane using an XCell II™ Blot Module (Invitrogen #EI9051) run at 30 V for 1 h in NuPAGE Transfer Buffer (Life Technologies #1904537). Following transfer, membranes were blocked by shaking for 1 h at room temperature with 5% non-fat dry milk in TBS. Blots were probed overnight at 4° C. with primary antibodies dissolved in 5% non-fat dry milk in TBS+0.1% Tween 20 (TBSt). The primary antibodies used were as follows: anti-human or anti-mouse recombinant LDHA purified sheep IgG (R & D Systems #AF7304), anti-pyruvate dehydrogenase E1-alpha subunit (phospho S293) rabbit polyclonal antibody (Abcam #ab92696), and anti-β-actin mouse monoclonal antibody clone AC-15 (Sigma #A1978). Following incubation with primary antibodies, blots were washed 4 times in TBSt and then incubated for 1 h at room temperature with secondary antibodies dissolved in TBSt. The secondary antibodies used were: rabbit anti-sheep IgG DyLight 800 (Thermo #SA5-10060), infrared Dye® 680RD goat anti-rabbit (LI-COR #926-68071), or infrared Dye® 680RD goat anti-mouse (LI-COR #926-68070). Following secondary antibody incubations, blots were washed with TBSt and imaged using an Odyssey® CLx Imaging System (LI-COR).

Metabolomics and 13C Labeling

CD8+ T cells were isolated from 6-week old C57BL/6 mouse spleens (StemCell #19853), activated for 48 h with anti-CD3+anti-CD28, washed, and replated for 48 h in medium alone or medium supplemented with human IL-2 or mouse IL-21. Cells were then washed with media supplemented with dialyzed fetal bovine serum ("FBS") (ThermoFischer #A3382001), replated in RPMI 1640 medium containing 10% dialyzed FBS, 1× Glutamax (ThermoFisher #35050061), 1 mM sodium pyruvate, 0.1% β-mercaptoethanol, and penicillin-streptomycin, and re-stimulated with same cytokine treatment for 5 h. For $^{13}C$ labelling, cells were instead replated in media containing 2 g/L $U^{13}C$-glucose (Cambridge Isotope Laboratories #CLM-1396) for 6 h. $3\times10^{6}$ cells/replicate (3-4 replicates/treatment) were then transferred to microcentrifuge tubes and centrifuged for 1 min at 6000×g. Room temperature PBS was added to wash cell pellets followed by another round of centrifugation for 1 min. Pellets were then immediately resuspended in 150 μl of ice cold extraction solvent (40:40:20 acetonitrile:methanol:water+0.5% formic acid) for 5 min. After incubation, 13.2 μl of 15% ammonium bicarbonate, was added and samples were centrifuged for 15 min at maximum speed at 4° C. Supernatant containing cellular metabolites was transferred to a fresh tube, frozen in dry ice, and stored at −80° C. Cell extracts were analyzed using a quadrupole-orbitrap mass spectrometer (Q Exactive, Thermo Fisher Scientific, San Jose, CA) coupled to hydrophilic interaction chromatography via electrospray ionization. LC separation was on a XBridge BEH Amide column (2.1 mm×150 mm, 2.5 μm particle size; Waters, Milford, MA) using a gradient of solvent A (20 mM ammonium acetate, 20 mM ammonium hydroxide in 95:5 water: acetonitrile, pH 9.45) and solvent B (acetonitrile). The flow rate was 150 μl/min, column temperature was 25° C., autosampler temperature was 5° C., and injection volume was 10 μL. The LC gradient was: 0 min, 90% B; 2 min, 85% B; 3 min, 75% B; 7 min, 75% B; 8 min, 70% B; 9 min, 70% B; 10 min, 50% B; 12 min, 50% B; 13 min, 25% B; 14 min, 25% B; 16 min, 0% B; 21 min, 0% B; 22 min, 90% B; 25 min, 90% B. Autosampler temperature was 5° C., and injection volume was 10 μl. The mass spectrometer was operated in negative ion mode to scan from m/z 70 to 1000 at 1 Hz and a resolving power of 140,000 45. Data were analyzed using EL-MAVEN software. Isotope labeling was corrected for natural 13C abundance47. Media measurements were acquired using a YSI 2900 Series Biochemical Analyzer (Xylem).

Mitochondrial Stress Test

The oxygen consumption rates (OCR) and extracellular acidification rates (ECAR) were recorded using a Seahorse XFe96 Analyzer (Agilent). Cells were washed and resuspended in Agilent XF Assay Medium supplemented with 25 mM glucose, 1 mM sodium pyruvate, and 2 mM L-Glutamine. Cells were plated on Seahorse Assay plates at $0.2\times10^{6}$ cells/well and during the assay were exposed to 1 μM oligomycin, 1.5 μM trifluoromethoxy carbonylcyanide phenylhydrazone ("FCCP"), 100 nM rotenone, and 1 μM antimycin A, as indicated.

RNA-Seq Analysis, Preparation and Bioinformatics Analysis

Total RNA was extracted using an RNA miniprep kit (Zymo Research), and 500 ng RNA was used for library preparation. RNA-Seq libraries were prepared using mRNA HyperPrep Kits (KK8580, Kapa Biosystems) and indexed with NEXTflex DNA Barcodes-24. After final amplification, samples were loaded to 2% E-Gel pre-cast gels (ThermoFisher), and 250 to 400 bp DNA fragments were recovered and purified with Zymoclean Gel DNA Recovery Kit (ThermoFisher). After quantification by Qubit (Invitrogen), barcoded samples were mixed and sequenced on an Illumina HiSeq3000 platform. Sequenced reads (50 bp, single end) were obtained with the Illumina CASAVA pipeline and mapped to the mouse genome mm10 (GRCm38, December 2011) using Bowtie 2.2.649 and Tophat 2.2.149. Only uniquely mapped reads were retained. Raw counts that fell on exons were calculated and normalized by using RPKM (Reads Per Kilobase per Million mapped reads). Differentially expressed genes were identified with the R Bioconductor package edgeR50, and the expression heat maps were generated with the R package "pheatmap". Metabolic genes were extracted from the KEGG pathway database, including those corresponding to Fatty Acid Biosynthesis/Degradation, Ox/Phos, Pyruvate metabolism, amino sugar and nucleotide sugar metabolism, pentose phosphate pathway, the citric acid cycle, and glycolysis/gluconeogenesis. Metabolic genes that overlapped with RNA-Seq data were subsequently shown in heat maps.

Real-Time PCR Assay

Total RNA was isolated as specified by the Direct-zol™ RNA MiniPrep kit (Zymo Research #R2052) and cDNA was synthesized with the 5× All-In-One RT MasterMix kit (abm #G590). Taqman probes were used for the RT-PCR measurements of Pfkm (Mm01309576 ml), Pgk1 (Mm00435617 ml), and Slc2a1 (Mm00441480_ml). The SYBR method was used for amplifying Ldha using forward primer 5'TATCTTAATGAAGGACTTGGCGGATGAG3' (SEQ ID NO: 1) and reverse primer 5'GGAGTTCGCAGTTACACAGTAGTC3' (SEQ ID NO: 2). All measurements were performed on a CFX96™ Real-Time System (Bio-Rad).

Flow Cytometric Analysis

Live cells were stained in FACS buffer containing 0.5% BSA and 0.02% sodium azide in PBS. Cells were stained at 4° C. for 30 min in darkness with anti-CD8 (53-6.7, BioLegend), anti-CD62L (MEL-14, BioLegend), anti-CD44 (IM7, BD Pharmingen), anti-Sca-1 (D7, Biolegend), and Live/Dead aqua (Invitrogen). After staining, cells were washed and analyzed on a BD LSRFortessa™ X-20 cytometer. For glucose uptake experiments, cultured cells were starved for 7 h in glucose-free media, then treated with a fluorescently-labeled glucose derivative (Cayman #600471) for 10 min, and assessed using a flow cytometer. All analyses were done using FlowJo software (TreeStar).

Electron Microscopy

Cells were stimulated as indicated and chemically fixed for 1 h with 2.5% glutaraldehyde and 1% formaldehyde in 0.12 M sodium cacodylate buffer, pH 7.4, for conventional transmission electron microscopy (TEM). Specimens were then post-fixed in 1% osmium tetroxide in cacodylate buffer, en bloc stained with 1% uranyl acetate, dehydrated in an ethanol series/propylene oxide and embedded in EMbed 812 resin (Electron Microscopy Sciences, Hatfield PA). Ultrathin sections (50-60 nm) were obtained using an EM UC7 ultramicrotome (Leica, Vienna, Austria). Sections were examined with a JEM-1200EX (JEOL USA) transmission electron microscope (accelerating voltage 80 keV) equipped with a bottom-mounted AMT 6 megapixel digital camera (Advanced Microscopy Techniques Corp). Mitochondrial area measurements were done using Fiji imaging software (ImageJ).

Mouse Tumor Model and Adoptive Transfer 3.5×105 hpg100 transduced B16 melanoma (B-16KVP) cells were subdermally injected into WT C57BL/6 mice. Tumors were allowed to grow for 10 days before antigen-specific CD8+ T cell transfer. Splenic pmel-1 CD8+ T cells were harvested from C57BL/6 mice (StemCell #19853) and cultured for 4 days in anti-CD3+anti-CD28 with either 100 IU/ml IL-2 or 100 ng/ml IL-21 with or without NCI-737 (1 μM). After 2 days, media, cytokine, and NCI-737 (where appropriate) were replenished. On day 4, 1×106 T cells were injected into the tail vein of tumor-bearing mice in conjunction with hgp-100 vaccinia virus. Subsequently, mice were intraperitoneally injected with 6 doses of IL-2 (1 μg/mouse twice/day) on days 0, 1, and 2 post adoptive transfer. Tumor growth was monitored over time until tumors exceeded 20 mm in dimension.

Statistics

Data sets were analyzed using Prism 7.0 software; shown is mean±SEM. Unless otherwise stated, data sets comparing IL-2, IL-21, and NC were analyzed for significance using one-way ANOVA and Tukey multiple comparison test, and statistics comparing IL-2 vs IL-2+NCI-737 and IL-21 vs IL-21+NCI-737 were performed using a two-tailed, unpaired Student's t-test. *p<0.05, p<0.01, *p<0.001, ****p<0.0001, and n.s., not significant. The metabolomics heatmap and PCA were was done using ClustVis51.

Example 1

This example provides a comparison of CD8+ T cells cultured in the presence of IL-2 and IL-21.

To compare the metabolic effects of IL-21 and IL-2 on mouse splenic CD8+ T cells, the cells were activated with anti-CD3+anti-CD28 for 48 h and then cultured them for 48 h with no cytokine (NC), IL-2, or IL-21 (FIG. 1A). IL-2-treated cells exhibited higher basal metabolism than IL-21-treated cells (FIG. 1B), with higher basal oxygen consumption rate (OCR) (FIG. 1C) and extracellular acidification rate ("ECAR") (FIG. 1D). IL-21-treated cells exhibited limited metabolic differences from cells cultured without exogenous cytokines (FIGS. 1C, D). This more quiescent state in IL-21-treated cells was consistent with preservation of mitochondrial spare respiratory capacity ("SRC") (FIG. 1E), which is a feature of memory T cells and correlates with their potential for expansion upon re-stimulation. In contrast, SRC was minimal in IL-2-treated cells (FIG. 1E). The major differences in ECAR between IL-2 and IL-21 were not evident at 4 or 12 h but were present by 24 h and greater at 48 h, with differences in OCR at 48 h as well (FIG. 5). IL-2 also induced more energetic basal metabolism in human CD8+ T cells compared to IL-21 (FIG. 6A), with higher OCR and ECAR, whereas IL-21 sustained a higher SRC (FIG. 6B). Because of these metabolic differences, electron microscopy was used to examine mitochondrial morphology, as metabolic reprogramming is accompanied by mitochondrial remodeling. For example, differentiation in effector T cells is associated with punctate mitochondria, loosely structured mitochondrial cristae, disrupted oxidative phosphorylation, and Warburg metabolism. After 48 h of anti-CD3+anti-CD28 activation, cells had mitochondria with tight cristae (FIG. 1F, top), indicative of the maintenance of redox chemistry and efficient oxidative phosphorylation. After 48 h of further culture in media or IL-21, cells retained tight mitochondrial cristae and similar morphology (FIG. 1F, middle two panels), but IL-2-treated cells had large dysmorphic mitochondria with loosely structured cristae (FIG. 1F, bottom; FIG. 7).

This example demonstrates the metabolic differences in cells expanded in the presence of IL-2 as compared to IL-21

Example 2

The comparative effects of IL-2 versus IL-21 were further assessed using RNA-Seq analysis.

As opposed to cells cultured without exogenous cytokines (no cytokine, NC), IL-2-induced expression of key glycolytic genes, including Slc2a1, encoding the glucose transporter GLUT1; Pgk1, encoding the enzyme involved in the first ATP generating step of glycolysis; Pfkm, a key regulator of glycolytic flux; and Ldha, encoding the most prominent isoform of lactate dehydrogenase (LDH) (FIG. 1G, arrows). Induction of these genes was confirmed by qRT-PCR (FIG. 8A). Without being bound by a particular theory, these genes had modestly IL-2-enhanced chromatin accessibility by ATAC-Seq (FIG. 8B), which is consistent with a transcriptional mechanism for the increased mRNA. The number of metabolic genes differentially expressed by IL-2 in comparison with NC control was much greater than differentially expressed by IL-21 versus NC (FIG. 1G). Despite phenotypic similarities between cells receiving no cytokine versus IL-21, IL-21-treated cells proliferated faster as assessed by fold-expansion (FIG. 9A) and CFSE dilution (Suppl. FIG. 5*b*), although IL-2 induced even greater expansion (FIG. 9A, B). Moreover, both IL-2- and IL-21-treated cells exhibited markedly higher viability than those receiving no cytokine (FIG. 9C, D).

This example demonstrates that IL-2 is pro-glycolytic and expands and disrupts mitochondria, whereas IL-21 is more limited in its metabolic effects but nevertheless can sustain cell survival.

Example 3

This example describes metabolomics analysis conducted on IL-2 and IL-21 treated cells.

Metabolomics analysis showed that IL-2-treated cells had the most distinctive metabolite composition, while cells treated with IL-21 or medium alone were more similar (FIG. 1H, FIG. 10A). Together with bioenergetic and transcriptomic data, this revealed that IL-2 and IL-21 differ in their regulation of key genes and metabolites involved in glycolysis.

The molecular and biochemical regulation of glucose and pyruvate were examined. Studies using a fluorescently-labeled glucose derivative coupled to flow cytometry revealed that IL-2-treated CD8+ T cells had higher glucose uptake capacity than cells treated with NC or IL-21 (FIG.

10B), but IL-2-treated cells had the lowest intracellular glucose (measured by LC-MS) (FIG. 10C). Without being bound by a particular theory, these results are consistent with rapid consumption via glycolysis and associated high levels of pyruvate (FIG. 10D) and lactate (FIG. 1I) and with the Ldha gene expression data (FIG. 1G, FIG. 8A). IL-2-treated cells had higher LDHA than IL-21-treated cells (FIG. 1J). The other major regulator of pyruvate entry into TCA, pyruvate dehydrogenase (PDH), is negatively regulated by IL-2, and the inactive, phosphorylated form of PDH was higher in IL-2 than in IL-21 and NC-treated cells (FIG. 10E), additionally showing that while IL-2 induces glycolysis and restricts pyruvate incorporation into the TCA cycle, IL-21 is metabolically more inert.

This example further demonstrates the metabolic differences between cells treated with IL-2 and IL-21.

Example 4

To rewire IL-2-induced metabolism, a small molecule inhibitor of LDH, denoted NCI-737, was used that inhibits both LDHA and LDHB isoforms (FIG. 10F). LDH activity maintains cytosolic levels of NAD+ and the NADH/NAD+ ratio to sustain glycolytic flux. NCI-737 treatment in IL-2- or IL-21-stimulated cells reduced lactate secretion (FIG. 2A) and glucose consumption (FIG. 2B). The lower lactic acid secretion was consistent with the color change of the pH indicator dye in the culture media (FIG. 11A). For IL-21 stimulated cells, NCI-737 treatment did not alter intracellular pyruvate levels (FIG. 2C), slightly raised the NADH/NAD+ ratio (FIG. 2D) and had little effect on metabolite levels (FIG. 2E), but for IL-2-treated cells, NCI-737 markedly increased intracellular pyruvate (FIG. 2C) and caused a ~100-fold increase in the NADH/NAD+ ratio (FIG. 2D). Furthermore, NCI-737 treatment lowered lactate in cells stimulated with either IL-2 or IL-21 (FIG. 11B). Consistent with the markedly increased pyruvate in cells treated with IL-2+NCI-737 (FIG. 2C), the lactate/pyruvate ratio was lower in these cells (FIG. 11C). Moreover, in the IL-2 setting, NCI-737 treatment most changed lactate, pyruvate, and NADH (FIG. 2F), which are direct substrates and products of LDH, but more than a 4-fold increase was also observed in glycolytic intermediates. Without being bound by a particular theory, this is presumably due to downstream inhibition of glycolysis, and in FGAR, an intermediate in purine biosynthesis. 2-hydroxyglutarate (2HG), which plays a key role in T cell differentiation and whose production in CD8+ T cells occurs substantially via LDH, was also decreased by NCI-737 (FIG. 2F). NCI-737 also globally affected gene expression induced by IL-21 and IL-2 (see principal component analysis of RNA-Seq data, FIG. 2G), with a greater effect for NCI-737 on metabolism-associated genes in cells treated with IL-2 than cells treated with IL-21 (FIG. 2H). Most genes differentially expressed by IL-21 versus IL-21+NCI-737 were not metabolism-associated genes, with many, for example, related to the cell cycle (FIG. 12A). Cells treated with IL-2+NCI-737 had a metabolic transcriptomic pattern more closely resembling that of cells treated with IL-21 as opposed to cells treated with IL-2 (FIG. 2H, Suppl. Table 1). As compared to IL-21, in the IL-2 context, NCI-737 had a greater effect on genes related to glycolysis and gluconeogenesis (FIG. 2H), and NCI-737 prevented the induction of Ldha by IL-2 (FIG. 2H, arrow), although levels of Ldhb were increased.

This example demonstrates the effects of introducing a lactate dehydrogenase inhibitor to cells to alter IL-2 and IL-21 induced metabolism.

Example 6

To further assess metabolic changes induced by LDH inhibition, a U-13C-glucose tracer study was performed on IL-21- and IL-2-treated T cells. NCI-737 had little effect on isotopomer distribution in IL-21-stimulated cells, but resulted in a higher relative contribution of glucose into the TCA cycle in IL-2-treated cells (FIG. 3A), as previously observed in cancer cells when LDHA was targeted. NCI-737 did not significantly alter basal OCR (FIG. 3B), SRC (FIG. 3C), or ECAR (FIG. 3D) in IL-21-treated cells, but significantly increased OCR and SRC and decreased ECAR in IL-2-treated cells (FIGS. 3B-D). Thus, NCI-737 limits pyruvate conversion to lactate and thereby favors pyruvate oxidation into the TCA cycle, promoting mitochondrial metabolism in IL-2-stimulated cells. In human CD8+ T cells (FIGS. 13A and 13B), NCI-737 had similar effects but with the following difference: it both decreased ECAR and raised SRC for both IL-21 and IL-2 (FIG. 13C).

This example demonstrates that blocking LDH alters metabolism in CD8+ T cells, by promoting pyruvate oxidation and entry into the TCA cycle, thereby making IL-2 act more like IL-21 and, especially in human T cells, further accentuating oxidative capacity even in IL-21-treated cells.

Example 7

To investigate whether LDH inhibition could reprogram CD8+ T cell function, a mouse model of adoptive cancer immunotherapy was used. In this regard, pmel-1 CD8+ T cells that recognize the shared melanoma-melanocyte differentiation antigen gp100 were transferred into C57BL/6 mice bearing subcutaneous B16 melanoma expressing a mutated gp100 antigen, B16KVP (FIG. 4A). LDH activity was inhibited only during the in vitro expansion phase. As has been reported in the art, when pmel-1 CD8+ T cells were activated with anti-CD3+anti-CD28, IL-2 was more potent than IL-21 in driving differentiation of CD44hiCD62Llo effector memory cells (FIG. 4B), but IL-21 treatment resulted in more CD44loCD62LhiSca1hi cells, typical of TSCM cells (FIG. 4B). NCI-737 restored TSCM cells in IL-2-treated cells to the levels observed with IL-21 and unexpectedly synergized with IL-21 to generate TSCM cells (FIG. 4B). Moreover, NCI-737 repressed IL-2- and IL-21-specific programs of exhaustion and senescence. For example, transcripts for IL-2-induced transcription factors associated with exhaustion, including Nr4a1, Nr4a2, Nrfa3, and Prdm1 (refs), were decreased by the addition of NCI-737 to levels similar to that observed in cells cultured with IL-21, and IL-21+NCI-737 treatment resulted in even lower expression of these transcripts (FIG. 14A). Similarly, transcripts for XBP1, which plays a key role in the unfolded protein response and can diminish antitumor efficacy of T cells in human ovarian cancer by regulating mitochondrial activity, was also induced by IL-2 but not IL-21, and its expression was inhibited by NCI-737 (FIG. 14A). Furthermore, transcripts for exhaustion markers Lag3, Pdcd1 (encoding PD1), Cd244 (encoding 2B4), and Havcr2 (encoding TIM3) that are induced by IL-21 were repressed by the addition of NCI-737 (FIG. 14A). Taken together, these phenotypic and transcriptomic data suggest that NCI-737 might be used to program CD8+ T cells that can mediate enhanced antitumor activity. Indeed, following adoptive transfer, both IL-2 and IL-21 conferred therapeutic advantage (individual tumor curves in FIG. 4C; summarized in FIG. 4D), with IL-21-treated cells more effective than IL-2-treated cells. However, in IL-2-treated cells, NCI-737 augmented the antitumor effect to the level of IL-21-treated cells (FIG. 4D), and cells generated with IL-21 and NCI-737 were the most potent (FIG. 4D). These antitumor effects corresponded to greater animal survival (FIG. 4E), revealing a major role for LDH in regulating CD8+ T cell fate decisions in response to IL-2 and IL-21 and that targeting LDH has therapeutic potential in adoptive T cell-based immunotherapy.

These examples demonstrate the enhanced antitumor activity conferred by adding NCI-737 to IL-2-treated cells during the in vitro priming/expansion phase underscores that lower LDH activity allows development of cells with enhanced tumor clearance. Without being bound by a particular theory, these results potentially explain the augmented antitumor responses by pmel-1 cells primed with IL-21. The further improvement of IL-21-treated cells when combined with NCI-737 versus IL-21 alone or IL-2+NCI-737 indicates that IL-21 has beneficial effects beyond sustaining low LDH activity, and antitumor efficacy and survival correlated with more pmel-1 TSCM cells prior to transfer. The fact that similar in vitro effects of NCI-737 were observed on human CD8+ T cells as well further underscores the potential therapeutic benefits of LDH inhibition in adoptive cell transfer-based immunotherapy.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for treating cancer in a mammal, the method comprising:

(a) obtaining an isolated population of T cells;

(b) preparing cultured T cells by culturing the isolated T cells ex vivo in the presence of a cytokine and a lactate dehydrogenase inhibitor; and (c) administering the cultured T cells to the mammal, wherein the lactate dehydrogenase inhibitor is defined by the structure:

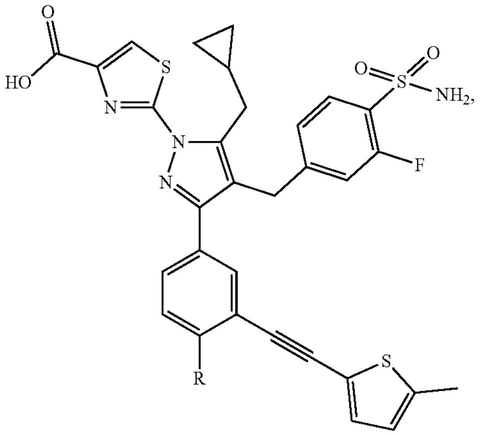

wherein R is F or H.

2. The method of claim 1, wherein R is F.

3. The method of claim 1, wherein R is H.

4. The method of claim 1, wherein the cytokine is IL-2.

5. The method of claim 1, wherein the cytokine is IL-21.

6. The method of claim 1, wherein the T cells are CD8+ T cells.

7. The method of claim 1, wherein the isolated population of T cells are obtained by harvesting the CD8+ T cells from the mammal.

8. The method of claim 7, wherein the T cells are harvested from the peripheral blood of the mammal.

9. The method of claim 7, wherein the mammal comprises a tumor and the T cells are harvested from a tumor sample taken from the mammal.

10. The method of claim 7, wherein the T cells are splenic.

11. The method of claim 1, wherein the cancer is melanoma.

12. The method of claim 1, wherein the T cells recognize an antigen expressed by the cancer cells.

13. The method of claim 12, wherein the antigen is gp100.

14. The method of claim 1, wherein the cultured T cells are administered intravenously to the mammal.

15. The method of claim 1, wherein the culturing of the T cells is further in the presence of one or more antibodies selected from the group consisting of an anti-CD3 antibody and an anti-CD28 antibody.

16. The method of claim 1, wherein the method further comprises administering a cytokine to the mammal after administering the cultured T cells to the mammal.

17. The method of claim 1, wherein the mammal is human.

18. The method of claim 1, wherein the cultured T cells are autologous to the mammal.

19. The method of claim 1, wherein the cultured T cells are allogeneic to the mammal.

20. The method of claim 1, wherein the method comprises expanding the number of isolated T cells in the presence of a lactate dehydrogenase inhibitor.

21. The method of claim 1, wherein the method comprises administering the cultured T cells to the mammal in an amount sufficient to reduce the number of cancer cells in the mammal or to reduce metastasis of the cancer cells in the mammal.

22. The method of claim 1, wherein culturing the isolated T cells in the presence of the lactate dehydrogenase inhibitor increases anti-tumor activity of the cultured T cells as compared to control cells, wherein the control cells are identical to the cultured T cells except that the control cells are not cultured in the presence of the lactate dehydrogenase inhibitor.

23. The method of claim 1, wherein the method further comprises administering IL-2 to the mammal after administering the cultured T cells to the mammal.

* * * * *

SEQUENCE LISTING

```
<160> NUMBER OF SEQ ID NOS: 2

<210> SEQ ID NO 1
<211> LENGTH: 28
<212> TYPE: DNA
<213> ORGANISM: Artificial Sequence
<220> FEATURE:
<223> OTHER INFORMATION: Synthetic

<400> SEQUENCE: 1

tatcttaatg aaggacttgg cggatgag                                          28


<210> SEQ ID NO 2
<211> LENGTH: 24
<212> TYPE: DNA
<213> ORGANISM: Artificial Sequence
<220> FEATURE:
<223> OTHER INFORMATION: Synthetic

<400> SEQUENCE: 2

ggagttcgca gttacacagt agtc                                              24
```